United States Patent
Tsvelikhovsky et al.

(10) Patent No.: US 10,392,338 B2
(45) Date of Patent: Aug. 27, 2019

(54) SPIROFURANONE COMPOUNDS, DERIVATIVES THEREOF AND PROCESSES FOR THEIR PREPARATION

(71) Applicant: Yissum Research Development Company of The Hebrew University of Jerusalem Ltd., Jerusalem (IL)

(72) Inventors: Dmitry Tsvelikhovsky, Jerusalem (IL); Avi Priel, Tel-Aviv (IL)

(73) Assignee: YISSUM RESEARCH DEVELOPMENT COMPANY, OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 15/546,348

(22) PCT Filed: Jan. 28, 2016

(86) PCT No.: PCT/IL2016/050098
§ 371 (c)(1),
(2) Date: Jul. 26, 2017

(87) PCT Pub. No.: WO2016/120879
PCT Pub. Date: Aug. 4, 2016

(65) Prior Publication Data
US 2018/0016221 A1    Jan. 18, 2018

Related U.S. Application Data

(63) Continuation of application No. PCT/IL2016/050098, filed on Jan. 28, 2016.

(30) Foreign Application Priority Data

Jan. 29, 2015  (IL) .......................... 236984

(51) Int. Cl.
| | |
|---|---|
| C07D 307/77 | (2006.01) |
| C07C 69/608 | (2006.01) |
| C07D 309/28 | (2006.01) |
| C07D 309/30 | (2006.01) |
| C07C 69/738 | (2006.01) |
| C07D 493/04 | (2006.01) |
| C07D 307/83 | (2006.01) |

(52) U.S. Cl.
CPC .......... *C07C 69/608* (2013.01); *C07C 69/738* (2013.01); *C07D 307/77* (2013.01); *C07D 307/83* (2013.01); *C07D 309/28* (2013.01); *C07D 309/30* (2013.01); *C07D 493/04* (2013.01); *C07C 2601/08* (2017.05); *C07C 2601/14* (2017.05); *C07C 2601/18* (2017.05)

(58) Field of Classification Search
CPC .................................................. C08D 307/83
See application file for complete search history.

(56) References Cited

FOREIGN PATENT DOCUMENTS

WO    WO 20051108362    11/2005

OTHER PUBLICATIONS

Brown et al, In vivo transformations of artemisinic acid in Artemisia annua plants, 2007, vol. 63, p. 9548-9566. (Year: 2007).*
Lansbury et al, Total synthesis of (−)arteannuin B, 1986, Tetrahedron Letters, vol. 27, No. 34, p. 3967-3970 (Year: 1986).*
Albarghouti et al. "Cascade Pd (II)-cataiyzed Wacker lactonization—Heck reaction: rapid assembly of spiranoid lactones." Chemical Communications 52.15 (2016): 3095-3098.
Anderson et al. "Synthesis of 1-azatricyclo [5.2. 1.04, 10] decane." The Journal of Organic Chemistry 43.1 (1978): 54-57.
Barriault et al. "Total synthesis of (+)-arteanniun M using the tandem oxy-Cope/ene reaction." Organic letters 3.12 (2001): 1925-1927.
Dauben et al. "Synthesis of (4.5. 5.5] fenestrane and a [4.4. 5.5] fenestrane derivative." Tetrahedron Letters 23.7 (1982): 711-714.
Julia et al. "Syntheses a l'aide de sulfones v (+)-methode de synthese generale de doubles liaisons" Tetrahedron Letters, Jan. 1, 1973:14(49):4833-6.
Lankri et al. "Palladium-Catalyzed Cascade Assembly of Tricyclic Spiroethers from Diene-Alcohol Precursors," The Journal of organic chemistry 82.18 (2017): 9452 9463.
Leonard et al. "Reductive Cyclization. A Method for the Synthesis of Tricyclic Compounds Possessing a Bridgehead Nitrogen1," Journal of the American Chemical Society 74.20 (1952): 5114-5118.
Mandell et al. "A Convenient Synthesis of Tricyclic 2-Quinolizidones1" The Journal of Organic Chemistry. Oct. 1964;29(10):3067-8.
Meissner et al. "Nonpeptide αvβ3 antagonists. Part 2: constrained glycyl amides derived from the RGD tripeptide." Bioorganic & medicinal chemistry letters 12.1 (2002): 25-29.
Mostinski et al. "Synthesis of Tricyclic Spiranoid Lactones via I2/Sm (II)-and I2/Pd (0)-Mediated Cyclizations of a Common Cycloalkylmethylene Precursor," The Journal of organic chemistry 80.21 (2015); 10464-10473.
Muthusamy et al. "1; 8-Diazabicyclo [5.4. 0] undec-7-ene (DBU): A powerful catalyst for the michael addition reaction of β-ketoesters to acrylates and enones" Synthetic communications. Jan. 1, 2002;32(21):3247-54.
Tzvetkov et al. "Synthesis of angularly fused cyclopentanoids and analogous tricycles via photoinduced ketyl radical/radical anion fragmentation—cyclization reactions" Tetrahedron. Oct. 15, 2007;63(42):10497-510.
Valerio et al. "Stereo-and Regioselective Synthesis of Tricyclic Spirolactones by Diastereoisomeric Differentiation of a Collective Key Precursor." Chemistry-A European Journal22.8 (2016): 2640-2647.
Zhang et al. "Application of RCM Reaction in the Construction of ABC Ring of Micrandilactone A" Organic letters. Jan. 5, 2006;8(1):107-10.

(Continued)

*Primary Examiner* — Karen Cheng
(74) *Attorney, Agent, or Firm* — Mark S. Cohen; Pearl Cohen Zedek Latzer Baratz LLP

(57) ABSTRACT

The present invention provides compounds comprising fused tricyclic backbone structure and processes for their preparation. The invention further provides compounds and compositions useful in the treatment of pain and any type of disorder or symptom associated therewith.

10 Claims, 16 Drawing Sheets

(56) References Cited

OTHER PUBLICATIONS

STN-Registry database (Dec. 5, 2005), compounds such as 89319-62-0, etc.

Mihelcic, J. et al. "Oxidative Cyclizations: The Asymmetric Synthesis of (-)-Alliacol A". Journal of the American Chemical Society (2004), vol. 126, No. 29, pp. 9106-9111.

* cited by examiner

SPIROFURANONE COMPOUNDS, DERIVATIVES THEREOF AND PROCESSES FOR THEIR PREPARATION

CROSS-REFERENCE TO RELATED APPLICATIONS

This application is a National Phase Application of PCT International Application No. PCT/IL2016/050098, International Filing Date Jan. 28, 2016, claiming priority of IL Patent Application No. 236984, filed Jan. 29, 2015, which are hereby incorporated by reference.

TECHNOLOGICAL FIELD

The present invention provides compounds comprising angularly fused tricyclic backbone structure and processes for their preparation. The invention further provides compounds and compositions useful in the treatment of pain and any type of disorder or symptom associated therewith.

BACKGROUND

Many important biochemical compounds and drugs of natural origin contain spirofuranone ring structures (FIG. 1). There are numerous examples of these structures among the carbohydrates, terpenoids, vitamins, alkaloids, glycosides, and antibiotics. The presence of tricyclic structures in such diverse types of compounds is strongly indicative of the profound effects that such structures exert on physiological activity, which is reflected in the robust efforts to identify useful therapeutic agents that possess these characteristics.

Numerous studies have led to a wide variety of modern drugs and potential pharmaceutical candidates that share the compact tricyclic systems, such as Alliacanes (displaying antimicrobial activity and inhibition of DNA synthesis in the ascetic form of Ehrlich carcinoma), Arteannuins (antimalarial agents), Allamancins (antileukemic activity), Teucrolins (possessing a range of biological activities including antioxidant, antisepsis, anti-inflammation, antipyretic, analgesic, and antifeedant activities), and many others (FIG. 1). Such a broad natural diversity and biological activity present in a wide spectrum of these systems make them extremely attractive targets for synthetic chemists. Listed below are several distinct examples of families of natural products, which all contain multiple tricyclic angularly fused furanone frames despite having different biological origins.

From a synthetic point of view, there has been sustained interest in the chemistry of all of the above-mentioned natural products over the past few decades. Analysis of their molecular structures shows a highly compacted carbon skeleton with an angularly fused tri-penta/hexa/hepta/octa- or macro-cycles of different oxidation states in each of the rings, which together present a real synthetic challenge.

Since these molecules are naturally produced (in plants, fungi, microbes, and marine organisms) in small quantities, there is great interest in mass-producing them through a synthetic pathway. Unfortunately, access to a large number of these target molecules and their structural analogues is either unknown or hindered by their multistep syntheses. Furthermore, many compounds can only be harvested from their natural source, which is a process that can be tedious, time consuming, and expensive, as well as being wasteful on the natural resource. For example the following natural compounds have no or very tedious and commercially limited total synthesis reported Teucrolins (3 family members), Chlorahololides, Multistalides, Chloamutilides, Sarcanolides (11 members), Arteannuins (7 family members) has reported syntheses of some members (8-13 steps), Jaborosalactone, Callilongisin B, Allamancins (9 family members)—reported total synthesis of some products, Alliacanes (9 family members)—although there are numerous approaches to this natural product family, only three syntheses have been completed to date.

Though elegant and creative, the existing target-oriented strategies require harsh conditions, protecting group manipulations, and purification after each synthetic step (with overall low yields). For example, in the most recent attempt (2003) K. D. Moeller and co-workers accomplished the total synthesis of Alliacol A in 14 steps, which provided the first synthetic access to this sesquiterpenoid natural product family.

It should also be noted that the number of structural analogues that can be obtained from total synthesis or harvesting is limited. Thus, there is an urgent need for an efficient, concise, and universal protocol to provide scientist with access to a diverse range of natural and artificial structural derivatives (potential therapeutic agents and drug candidates).

There is therefore a long awaited need in the industry to provide a general or common approach towards the construction of naturally occurring complex structures such as quaternary carbon-centered tricyclic spiranoid lactones and natural and/or none natural derivatives thereof.

The present invention thus provides a common synthetic strategy using simple production steps for producing the tricyclic skeletons in a rapid and efficient manner.

General Description

In the first aspect the invention provides a compound of the general formula (I), including any stereoisomer thereof:

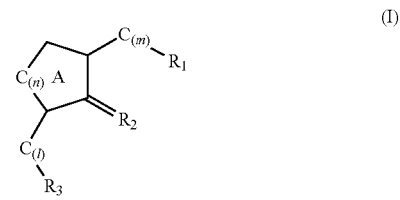

(I)

wherein

Ring A is optionally a saturated (having only sigma bonds between the carbon atoms) or unsaturated (having at least one double or triple bonds between two adjacent carbon atoms) ring having optionally at least one heteroatom (thus making ring A a heterocyclic ring); and is optionally substituted by at least one group selected from straight or branched $C_1$-$C_{10}$ alkyl, straight or branched $C_2$-$C_{10}$ alkenyl, straight or branched $C_2$-$C_{10}$ alkynyl, CN, —$OR_4$, —$NR_5R_6$, —C(=O)$R_7$, halogen;

$R_4$, $R_5$ and $R_6$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_7$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$)alkyl (e.g. $C_1$-$C_{10}$ alkoxy), $NH_2$, amine;

n is an integer selected from 1-10;

—$C_{(n)}$— is selected from a straight or branched alkylene, straight or branched alkenylene, straight or branched alkynylene; optionally interrupted by at least one heteroatom (thus making ring A a heterocyclic ring);

m is an integer selected from 1-10;

—$C_{(m)}$— is selected from a straight or branched alkylene, straight or branched alkenylene, straight or branched alkynylene; optionally interrupted by at least one heteroatom;

$R_1$ is selected from —C(=O)$R_8$, —C(=S)$R_9$, —C(=P)$R_{10}$, —C(=C$R_{11}R_{12}$)$R_{13}$, straight or branched $C_2$-$C_{10}$ alkenyl, straight or branched $C_2$-$C_{10}$ alkynyl;

each of $R_8$, $R_9$, $R_{10}$, $R_{11}$, $R_{12}$ and $R_{13}$ are independently is selected from a group consisting of OH, —O$R_{14}$, —NH$_2$, —NH$R_{15}$, —N$R_{16}R_{17}$;

each of $R_{14}$, $R_{15}$, $R_{16}$ and $R_{17}$ are independently selected from straight or branched $C_1$-$C_{10}$ alkyl;

$R_2$ is selected from O, S, C$R_{18}R_{19}$;

each of $R_{18}$ and $R_{19}$ is independently selected from H, straight or branched $C_1$-$C_{10}$ alkyl, halogen, $CF_3SO_3$, OH, $C_1$-$C_{10}$ alkoxy;

l is an integer selected from 1-10;

—$C_{(l)}$— is selected from a straight or branched alkylene, straight or branched alkenylene, straight or branched alkynylene; optionally interrupted by at least one heteroatom;

$R_3$ is selected from C(=O)$R_{20}$, O$R_{21}$, C(=O)O$R_{22}$, CN, $CF_3SO_3$, straight or branched $C_2$-$C_{10}$ alkenyl, straight or branched $C_2$-$C_{10}$ alkynyl;

each of alkenyl or alkylnyl groups are optionally substituted by at least one group selected from C(=O)$R_{23}$, O$R_{24}$, halogen, $CF_3SO_3$;

each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkyl (e.g. $C_1$-$C_{10}$ alkoxy), NH$_2$, amine (e.g. any primary —NHR', secondary —NR'R" or tertiary amine —N+R'R"R"', wherein R', R", R"' are each independently a straight or branched $C_1$-$C_{10}$alkyl).

The invention further provides a compound of the general formula (I), including any stereoisomer thereof:

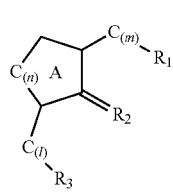

(I)

wherein

Ring A is optionally a saturated or unsaturated ring having optionally at least one heteroatom; and is optionally substituted by at least one group selected from straight or branched $C_1$-$C_{10}$ alkyl, straight or branched $C_2$-$C_{10}$ alkenyl, straight or branched $C_2$-$C_{10}$ alkynyl, CN, —O$R_4$, —N$R_5R_6$, —C(=O)$R_7$, halogen;

$R_4$, $R_5$ and $R_6$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_7$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$)alkyl, NH$_2$, amine;

n is an integer selected from 1-10;

—$C_{(n)}$— is selected from a straight or branched alkylene, straight or branched alkenylene, straight or branched alkynylene; optionally interrupted by at least one heteroatom;

m is an integer selected from 1-10;

—$C_{(m)}$— is selected from a straight or branched alkylene, straight or branched alkenylene, straight or branched alkynylene; optionally interrupted by at least one heteroatom;

$R_1$ is selected from —C(=O)$R_8$, —C(=S)$R_9$, —C(=P)$R_{10}$, —C(=C$R_{11}R_{12}$)$R_{13}$, straight or branched $C_2$-$C_{10}$ alkenyl, straight or branched $C_2$-$C_{10}$ alkynyl;

each of $R_8$, $R_9$, $R_{10}$, $R_{11}$, $R_{12}$ and $R_{13}$ are independently is selected from a group consisting of OH, —O$R_{14}$, —NH$_2$, —NH$R_{15}$, —N$R_{16}R_{17}$;

each of $R_{14}$, $R_{15}$, $R_{16}$ and $R_{17}$ are independently selected from straight or branched $C_1$-$C_{10}$ alkyl;

$R_2$ is selected from O, S, C$R_{18}R_{19}$;

each of $R_{18}$ and $R_{19}$ is independently selected from H, straight or branched $C_1$-$C_{10}$ alkyl, halogen, $CF_3SO_3$, OH, $C_1$-$C_{10}$ alkoxy;

l is an integer selected from 1-10;

—$C_{(l)}$— is selected from a straight or branched alkylene, straight or branched alkenylene, straight or branched alkynylene; optionally interrupted by at least one heteroatom;

$R_3$ is selected from C(=O)$R_{20}$, O$R_{21}$, C(=O)O$R_{22}$, CN, $CF_3SO_3$, straight or branched $C_2$-$C_{10}$ alkenyl, straight or branched $C_2$-$C_{10}$ alkynyl;

each of alkenyl or alkylnyl groups are optionally substituted by at least one group selected from C(=O)$R_{23}$, O$R_{24}$, halogen, $CF_3SO_3$;

each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, NH$_2$, amine;

provided that when $R_2$ is O, $R_3$ is selected from C(=O)$R_{20}$, O$R_{21}$, C(=O)O$R_{22}$, $CF_3SO_3$, straight or branched $C_2$-$C_{10}$ alkenyl, straight or branched $C_2$-$C_{10}$ alkynyl; each of alkenyl or alkylnyl groups are optionally substituted by at least one group selected from C(=O)$R_{23}$, O$R_{24}$, halogen, $CF_3SO_3$.

The invention further provides a compound of the general formula (I), including any stereoisomer thereof:

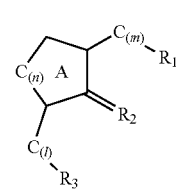

(I)

wherein

Ring A is optionally a saturated or unsaturated ring having optionally at least one heteroatom; and is optionally substituted by at least one group selected from straight or branched $C_1$-$C_{10}$ alkyl, straight or branched $C_2$-$C_{10}$ alkenyl, straight or branched $C_2$-$C_{10}$ alkynyl, CN, —O$R_4$, —N$R_5R_6$, —C(=O)$R_7$, halogen;

$R_4$, $R_5$ and $R_6$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_7$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$)alkyl, NH$_2$, amine;

n is an integer selected from 1-10;

—$C_{(n)}$— is selected from a straight or branched alkylene, straight or branched alkenylene, straight or branched alkynylene; optionally interrupted by at least one heteroatom;

m is an integer selected from 1-10;

—$C_{(m)}$— is selected from a straight or branched alkylene, straight or branched alkenylene, straight or branched alkynylene; optionally interrupted by at least one heteroatom;

$R_1$ is selected from —C(=O)$R_8$, —C(=S)$R_9$, —C(=P)$R_{10}$, —C(=C$R_{11}R_{12}$)$R_{13}$, straight or branched $C_2$-$C_{10}$ alkenyl, straight or branched $C_2$-$C_{10}$ alkynyl;

each of $R_8$, $R_9$, $R_{10}$, $R_{11}$, $R_{12}$ and $R_{13}$ are independently is selected from a group consisting of OH, —O$R_{14}$, —NH$_2$, —NH$R_{15}$, —N$R_{16}R_{17}$;

each of $R_{14}$, $R_{15}$, $R_{16}$ and $R_{17}$ are independently selected from straight or branched $C_1$-$C_{10}$ alkyl;

$R_2$ is selected from S, C$R_{18}R_{19}$;

each of $R_{18}$ and $R_{19}$ is independently selected from H, straight or branched $C_1$-$C_{10}$ alkyl, halogen, CF$_3$SO$_3$, OH, $C_1$-$C_{10}$ alkoxy;

l is an integer selected from 1-10;

—$C_{(l)}$— is selected from a straight or branched alkylene, straight or branched alkenylene, straight or branched alkynylene; optionally interrupted by at least one heteroatom;

$R_3$ is selected from C(=O)$R_{20}$, O$R_{21}$, C(=O)O$R_{22}$, CN, CF$_3$SO$_3$, straight or branched $C_2$-$C_{10}$ alkenyl, straight or branched $C_2$-$C_{10}$ alkynyl;

each of alkenyl or alkylnyl groups are optionally substituted by at least one group selected from C(=O)$R_{23}$, O$R_{24}$, halogen, CF$_3$SO$_3$;

each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, NH$_2$, amine.

In some embodiments Ring A is a saturated 5, 6, 7, or 8 member ring (thus the ring consists of 5, 6, 7 or 8 atoms connected to each other with saturated single bonds only). In other embodiments Ring A is an unsaturated 5, 6, 7 or 8 member ring (thus the ring comprises at least one unsaturated bond within the ring structure. Said unsaturated bond can be a double and/or a triple bond between any two atoms in the ring). In further embodiments Ring A is a 5-7 member ring having at least one heteroatom (thus said ring comprises at least one atom that is different than carbon being selected from O, N or S at any position in the ring. When valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

The term "—$C_{(n)}$—" as used herein refers to a straight or branched hydrocarbon chain that can be saturated (i.e. having only single bonds connecting the atoms in the chain) or unsaturated (i.e. having at least one unsaturated bond, double or triple bond, connecting the atoms in the ring), having m carbon atoms. "—$C_{(n)}$—" chain can be optionally interrupted by at least one heteroatom, thus any two carbon atoms in the chain can be interrupted with at least one heteroatom between them (for example . . . —C—N—C— . . . ). Said heteroatom selected from O, N, S, P, when valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

The term "—$C_{(m)}$—" as used herein refers to a straight or branched hydrocarbon chain that can be saturated (i.e. having only single bonds connecting the atoms in the chain) or unsaturated (i.e. having at least one unsaturated bond, double or triple bond, connecting the atoms in the ring), having m carbon atoms. "—$C_{(m)}$-" chain can be optionally interrupted by at least one heteroatom, thus any two carbon atoms in the chain can be interrupted with at least one heteroatom between them (for example . . . —C—N—C— . . . ). Said heteroatom selected from O, N, S, P, when valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

In some embodiments, —$C_{(m)}$— is selected from a $C_1$-$C_{10}$ straight or branched alkylene, $C_2$-$C_{10}$ straight or branched alkenylene, $C_2$-$C_{10}$ straight or branched alkynylene. In some further embodiments, —$C_{(m)}$— is a $C_1$-$C_{10}$ straight or branched alkylene.

In some embodiments, $R_1$ is —C(=O)$R_8$. In other embodiments, $R_1$ is —C(=O)O$R_{14}$.

In some embodiments, $R_2$ is O. In some other embodiments, $R_2$ is CH$_2$.

The term "—$C_{(l)}$—" as used herein refers to a straight or branched hydrocarbon chain that can be saturated (i.e. having only single bonds connecting the atoms in the chain) or unsaturated (i.e. having at least one unsaturated bond, double or triple bond, connecting the atoms in the ring), having 1 carbon atoms. "—$C_{(l)}$—" chain can be optionally interrupted by at least one heteroatom, thus any two carbon atoms in the chain can be interrupted with at least one heteroatom between them (for example . . . —C—N—C— . . . ). Said heteroatom selected from O, N, S, P, when valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

In some embodiments, —$C_{(l)}$— is selected from a $C_1$-$C_{10}$ straight or branched alkylene, $C_2$-$C_{10}$ straight or branched alkenylene, $C_2$-$C_{10}$ straight or branched alkynylene. In other embodiments, —$C_{(l)}$— is a $C_1$-$C_{10}$ straight or branched alkylene.

In some embodiments, $R_3$ is a straight or branched $C_2$-$C_{10}$ alkenyl optionally substituted by at least one group selected from —C(=O)$R_{20}$, O$R_{21}$, halogen and CF$_3$SO$_3$. In some further embodiments, $R_3$ is a straight or branched $C_2$-$C_{10}$ alkynyl optionally substituted by at least one group selected from —C(=O)$R_{20}$, O$R_{21}$, halogen and CF$_3$SO$_3$. In further embodiments, $R_3$ is —C(=O)$R_{20}$.

In some embodiments, the compound of the invention has the general formula (II):

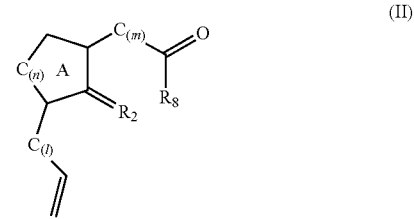

(II)

including any stereoisomer thereof, wherein $R_2$, $R_8$, $C_{(n)}$, n, $C_{(m)}$, m, $C_{(l)}$ and l are as defined herein above.

In some embodiments, the compound of the invention has the general formula (III):

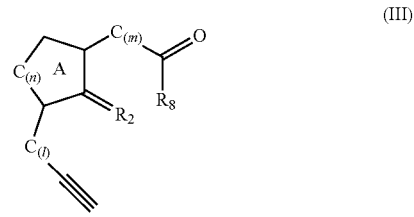

(III)

including any stereoisomer thereof, wherein $R_2$, $R_8$, $C_{(n)}$, n, $C_{(m)}$, m, $C_{(l)}$ and l are as defined herein above.

In further embodiments, the compound of the invention has the general formula (IV)

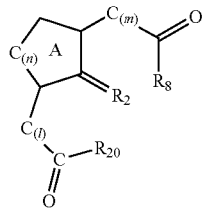

(IV)

including any stereoisomer thereof, wherein $R_2$, $R_8$, $R_{20}$, $C_{(n)}$, n, $C_{(m)}$, m, $C_{(l)}$ and l are as defined herein above.

In some further embodiments, a compound of the invention has the general formula (V):

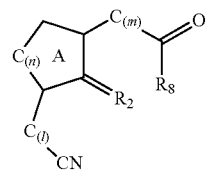

(V)

including any stereoisomer thereof, wherein $R_2$, $R_8$, $C_{(n)}$, n, $C_{(m)}$, m, $C_{(l)}$ and l are as defined herein above.

In some further embodiments, a compound of the invention has the general formula (VI):

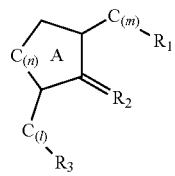

(VI)

including any stereoisomer thereof, wherein $R_1$, $R_2$, $R_3$, $C_{(n)}$, n, $C_{(m)}$, m, $C_{(l)}$ and l are as defined herein above.

In some further embodiments, a compound of the invention has the general formula (VII)

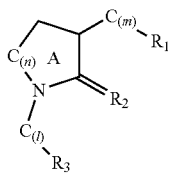

(VII)

including any stereoisomer thereof, wherein $R_1$, $R_2$, $R_3$, $C_{(n)}$, n, $C_{(m)}$, m, $C_{(l)}$ and l are as defined herein above.

In some further embodiments, a compound of the invention has the general formula (VIII)

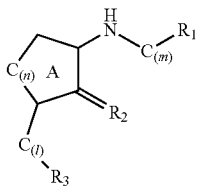

(VIII)

including any stereoisomer thereof, wherein $R_1$, $R_2$, $R_3$, $C_{(n)}$, n, $C_{(m)}$, m, $C_{(l)}$ and l are as defined herein above.

In some further embodiments, a compound of the invention has the general formula (IX)

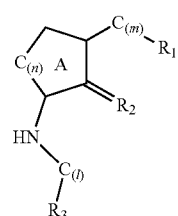

(IX)

including any stereoisomer thereof, wherein $R_1$, $R_2$, $R_3$, $C_{(n)}$, n, $C_{(m)}$, m, $C_{(l)}$ and l are as defined herein above.

In some further embodiments, a compound of the invention has the general formula (X)

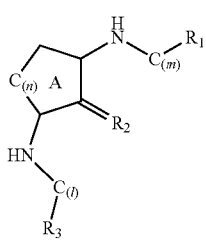

(X)

including any stereoisomer thereof, wherein $R_1$, $R_2$, $R_3$, $C_{(n)}$, n, $C_{(m)}$, m, $C_{(l)}$ and l are as defined herein above.

The invention further provides, a process for the preparation of a compound of general formula (I) as defined herein above, comprising the step of:

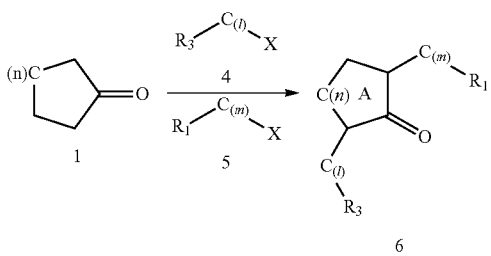

wherein $R_1$, $R_2$, $R_3$, $R_4$ and $C_{(n)}$, n, $C_{(m)}$, m, $C_{(l)}$ and l are as defined therein and X is selected from a halogen and straight or branched $C_2$-$C_{20}$ alkene.

The process defined herein above includes the substitution of —$C_{(m)}$—$R_1$ and —$C_{(l)}R_3$ on the cycloketone ring using any process known in the art for alkylating a cycloketone reagent. In some embodiments, said process is conducted in the presence of at least one of LDA, pyrrolidine and hydrazine.

In one embodiment, said process comprises the step of:

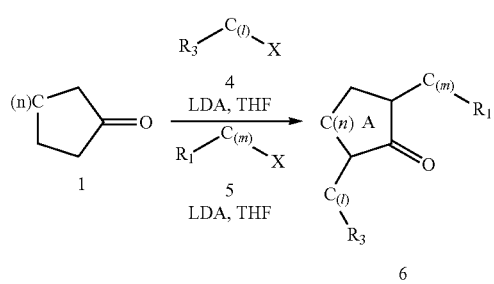

In one embodiment, said process comprises the steps of:

Step 1

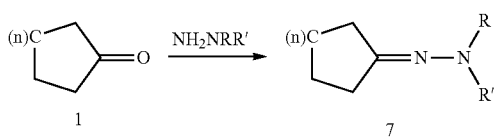

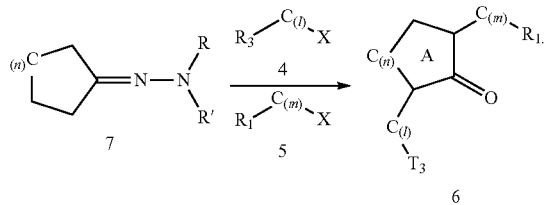

In another aspect the invention provides a process for the preparation of a compound as defined in claim 1, comprising the steps of:

Step 1

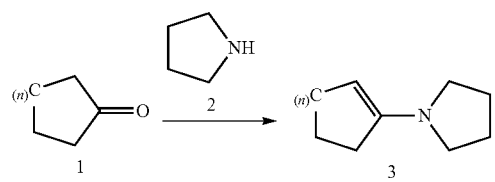

Step 2

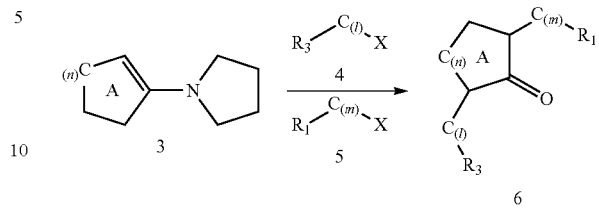

wherein $R_1$, $R_2$, $R_3$, $R_4$ and n, m and l are as defined therein and X is selected from a halogen and straight or branched $C_2$-$C_{20}$ alkene. In some embodiments, Step 1 is performed in the presence of MeCN. In some other embodiments, Step 2 is performed in the presence of MeCN. In some embodiments, Step 2 is performed in a single pot. In some embodiments, Step 1 and Step 2 are performed in a single pot. In further embodiments, Step 2 is performed in the presence of at least one Hunig's base. In yet further embodiments, compounds 4 and 5 are added simultaneously or consecutively. In other embodiments, compound 4 is added thereafter compound 5 is added in the presence of at least one Hunig's base.

In other embodiments, the process of the invention further comprises the step of:

Step 3

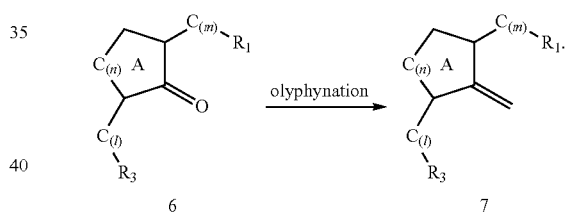

The olyfination process includes any process that reduces the keton moiety of compound 6 to the corresponding olefine. In some embodiments, said olyfination is performed under Wittig reaction conditions (using a Witting reagent such as for example a triphenyl phosphonium ylide). In other embodiments, said olyfination is performed under Julia reaction conditions (known as the Julia olefination or Julia-Lythgoe olefination using as an olefination reagent phenyl sulfones, see in Julia, M.; Paris, J.-M. *Tetrahedron Lett.* 1973, 14, 4833-4836 incorporated herein by reference).

In another aspect, the invention provides a compound having the general formula (XI), including any stereoisomer thereof:

(XI)

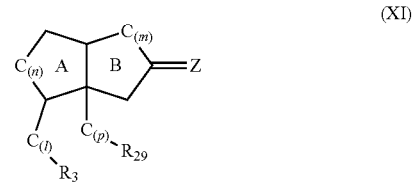

wherein

Ring A is optionally a saturated or unsaturated ring having optionally at least one heteroatom; and is optionally substituted by at least one group selected from straight or branched $C_1$-$C_{10}$ alkyl, straight or branched $C_2$-$C_{10}$ alkenyl, straight or branched $C_2$-$C_{10}$ alkynyl, CN, —$OR_4$, —$NR_5R_6$, —$C(=O)R_7$, halogen;

$R_4$, $R_5$ and $R_6$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_7$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$)alkyl, $NH_2$, amine;

n is an integer selected from 1-10; —$C_{(n)}$— is selected from a straight or branched alkylene, straight or branched alkenylene, straight or branched alkynylene; optionally interrupted by at least one heteroatom;

Ring B is optionally a saturated or unsaturated ring having optionally at least one heteroatom; and is optionally substituted by at least one group selected from straight or branched $C_1$-$C_{10}$ alkyl, straight or branched $C_2$-$C_{10}$ alkenyl, straight or branched $C_2$-$C_{10}$ alkynyl, CN, —$OR_{25}$, —$NR_{26}R_{27}$, —$C(=O)R_{28}$, halogen;

$R_{25}$, $R_{26}$ and $R_{27}$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_{28}$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$)alkyl, $NH_2$, amine;

m is an integer selected from 1-10; —$C_{(l)}$— is selected from a straight or branched alkylene, straight or branched alkenylene, straight or branched alkynylene; optionally interrupted by at least one heteroatom;

l is an integer selected from 1-10; —$C_{(l)}$— is selected from a straight or branched alkylene, straight or branched alkenylene, straight or branched alkynylene; optionally interrupted by at least one heteroatom;

$R_3$ is selected from $C(=O)R_{20}$, $OR_{21}$, $C(=O)OR_{22}$, CN, $CF_3SO_3$, straight or branched $C_2$-$C_{10}$ alkenyl, straight or branched $C_2$-$C_{10}$ alkynyl;

each of alkenyl or alkylnyl groups are optionally substituted by at least one group selected from $C(=O)R_{23}$, $OR_{24}$, halogen, $CF_3SO_3$;

each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, $NH_2$, amine;

p is an integer selected from 1-10;

—$C_{(p)}$— is selected from a straight or branched alkylene, straight or branched alkenylene, straight or branched alkynylene; optionally interrupted by at least one heteroatom;

$R_{29}$ is selected from a halogen, $M_1X$, $M_2LX$, $C(=O)R_{30}$, $OR_{31}$, $C(=O)OR_{32}$, $CF_3SO_3$, straight or branched $C_2$-$C_{10}$ alkenyl, straight or branched $C_2$-$C_{10}$ alkynyl; each of alkenyl or alkylnyl groups are optionally substituted by at least one group selected from a halogen, $C(=O)R_{33}$, $OR_{34}$, $CF_3SO_3$;

each of $R_{30}$, $R_{31}$, $R_{32}$, $R_{33}$ and $R_{34}$ is independently selected from H, OH, straight or branched $C_1$-$C_{10}$ alkyl, straight or branched $C_1$-$C_{10}$ alkoxy;

$M_1$ is selected from Zn, Mg; $M_2$ is selected from Pd, Cu; L is a ligand; X is a halogen;

Z is selected from O, $CR_{35}R_{36}$ wherein $R_{35}$ and $R_{36}$ are independently selected from H, halogen, OH, $C_1$-$C_{10}$alkoxy, $NH_2$, CN, amide, straight or branched $C_1$-$C_{10}$ alkyl.

In some embodiments Ring A is a saturated 5, 6, 7, or 8 member ring (thus the ring consists of 5, 6, 7 or 8 atoms connected to each other with saturated single bonds only). In other embodiments Ring A is an unsaturated 5, 6, 7 or 8 member ring (thus the ring comprises at least one unsaturated bond within the ring structure. Said unsaturated bond can be a double and/or a triple bond between any two atoms in the ring). In further embodiments Ring A is a 5-7 member ring having at least one heteroatom (thus said ring comprises at least one atom that is different than carbon being selected from O, N or S at any position in the ring. When valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

In some embodiments Ring B is a saturated 5, 6, 7, or 8 member ring (thus the ring consists of 5, 6, 7 or 8 atoms connected to each other with saturated single bonds only). In other embodiments Ring B is an unsaturated 5, 6, 7 or 8 member ring (thus the ring comprises at least one unsaturated bond within the ring structure. Said unsaturated bond can be a double and/or a triple bond between any two atoms in the ring). In further embodiments Ring B is a 5-7 member ring having at least one heteroatom (thus said ring comprises at least one atom that is different than carbon being selected from O, N or S at any position in the ring. When valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

In some embodiments, Ring A and Ring B is independently a saturated or unsaturated 5, 6, 7 or 8 member ring. In some further embodiments, Ring A and Ring B comprises a heteroatom. In some other embodiments, said heteroatom is selected from O, S, NH, $NR_{37}$ wherein $R_{37}$ is a straight or branched $C_1$-$C_{10}$ alkyl. In some embodiments, Ring B comprises said heteroatom. In other embodiments, said heteroatom is O. In other embodiments, said heteroatom is $NR_{37}$.

In some embodiments, a compound of the invention has the general formula (XII), including any stereoisomer thereof:

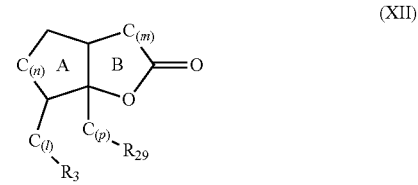

(XII)

$R_3$, $R_{29}$, $C_{(n)}$, n, $C_{(m)}$, m, $C_{(l)}$, l, $C_{(p)}$, p are as defined herein above.

In some embodiments, $R_{29}$ is selected from halogen, Pd(0)LX, ZnX, MgX, Cu(L)X.

In other embodiments, $R_3$ is selected from $C(=O)R_{20}$, $OR_{21}$, $C(=O)OR_{22}$, $CF_3SO_3$, straight or branched $C_2$-$C_{10}$ alkenyl, straight or branched $C_2$-$C_{10}$ alkynyl; each of alkenyl or alkylnyl groups are optionally substituted by at least one group selected from $C(=O)R_{23}$, $OR_{24}$, halogen, $CF_3SO_3$; each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, $NH_2$, amine (the term amine includes any primary, secondary, tertieary or quartenary amine each independently substituted with H, straight or branched $C_1$-$C_{10}$ alkyl, straight or branched $C_2$-$C_{10}$ alkenyl, straight or branched $C_2$-$C_{10}$ alkynyl).

In another aspect the invention provides the use of a compound of general formula (I), as defined hereinabove in all embodiments thereof, in the process comprising a angular cyclization step of:

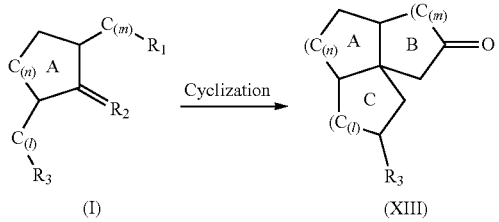

(I)

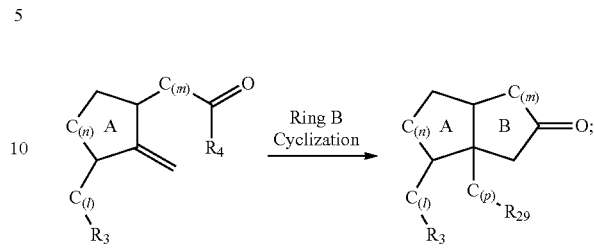

(XIII)

wherein $R_1$, $R_2$, $R_3$, n, m, l, are as defined above; Ring A, Ring B and Ring C are optionally a saturated or unsaturated ring having optionally at least one heteroatom; and each is optionally substituted by at least one group selected from branched $C_1$-$C_{10}$ alkyl, straight or branched $C_2$-$C_{10}$ alkenyl, straight or branched $C_2$-$C_{10}$ alkynyl, CN, —$OR_4$, —$NR_5R_6$, —C(=O)$R_7$, halogen;

$R_4$, $R_5$ and $R_6$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_7$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$)alkyl, $NH_2$, amine.

In some embodiments Ring A is a saturated 5, 6, 7, or 8 member ring (thus the ring consists of 5, 6, 7 or 8 atoms connected to each other with saturated single bonds only). In other embodiments Ring A is an unsaturated 5, 6, 7 or 8 member ring (thus the ring comprises at least one unsaturated bond within the ring structure. Said unsaturated bond can be a double and/or a triple bond between any two atoms in the ring). In further embodiments Ring A is a 5-7 member ring having at least one heteroatom (thus said ring comprises at least one atom that is different than carbon being selected from O, N or S at any position in the ring. When valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

In some embodiments Ring B is a saturated 5, 6, 7, or 8 member ring (thus the ring consists of 5, 6, 7 or 8 atoms connected to each other with saturated single bonds only). In other embodiments Ring B is an unsaturated 5, 6, 7 or 8 member ring (thus the ring comprises at least one unsaturated bond within the ring structure. Said unsaturated bond can be a double and/or a triple bond between any two atoms in the ring). In further embodiments Ring B is a 5-7 member ring having at least one heteroatom (thus said ring comprises at least one atom that is different than carbon being selected from O, N or S at any position in the ring. When valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

In some embodiments Ring C is a saturated 5, 6, 7, or 8 member ring (thus the ring consists of 5, 6, 7 or 8 atoms connected to each other with saturated single bonds only). In other embodiments Ring C is an unsaturated 5, 6, 7 or 8 member ring (thus the ring comprises at least one unsaturated bond within the ring structure. Said unsaturated bond can be a double and/or a triple bond between any two atoms in the ring). In further embodiments Ring C is a 5-7 member ring having at least one heteroatom (thus said ring comprises at least one atom that is different than carbon being selected from O, N or S at any position in the ring. When valency permits heteroatom is substituted with one or more H, straight or branched $C_1$-$C_{10}$ alkyl, straight or branched $C_2$-$C_{10}$ alkenyl, straight or branched $C_2$-$C_{10}$ alkynyl.

In some embodiments, said cyclization step comprises the steps of:

Step 4

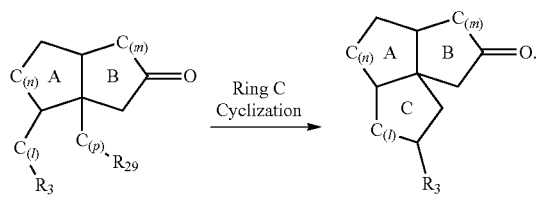

and

Step 5

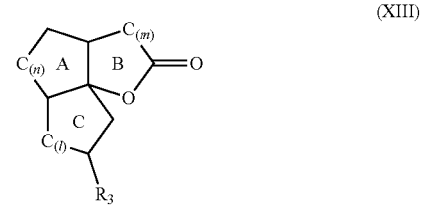

including any stereoisomers thereof, wherein $R_3$, $R_4$, $R_{29}$, $C_{(n)}$, n, $C_{(m)}$, m, $C_{(l)}$, l, $C_{(p)}$ and p are as defined herein above.

In some further embodiments, compound of formula (XIII) is:

(XIII)

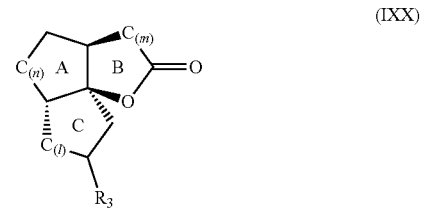

including any stereoisomer thereof, wherein $R_3$, $C_{(n)}$, n, $C_{(m)}$, m, $C_{(l)}$ and l are as defined herein above.

The invention provides a compound of general formula (XIII) wherein n=m=l=1, including any stereoisomer thereof.

In some embodiments, the invention provides a compound of general formula (IXX):

(IXX)

wherein $R_3$, $C_{(n)}$, n, $C_{(m)}$, m, $C_{(l)}$ and l are as defined herein above. In some embodiments n=m=l=1.

In some embodiments, the invention provides a compound of general formula (XX):

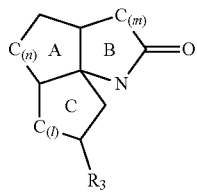

(XX)

including any stereoisomer thereof, wherein $R_3$, $C_{(n)}$, n, $C_{(m)}$, m, $C_{(l)}$ and l are as defined herein above.

The invention further provides a composition comprising a compound of general formula (XIV):

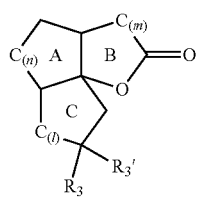

(XIV)

wherein

Ring A is optionally a saturated or unsaturated ring having optionally at least one heteroatom; and is optionally substituted by at least one group selected from straight or branched $C_1$-$C_{10}$ alkyl, straight or branched $C_2$-$C_{10}$ alkenyl, straight or branched $C_2$-$C_{10}$ alkynyl, CN, —$OR_4$, —$NR_5R_6$, —C(=O)$R_7$, halogen;

$R_4$, $R_5$ and $R_6$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_7$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$) alkyl, $NH_2$, amine;

n is an integer selected from 1-10;

—$C_{(n)}$— is selected from a straight or branched alkylene, straight or branched alkenylene, straight or branched alkynylene; optionally interrupted by at least one heteroatom;

m is an integer selected from 1-10;

—$C_{(m)}$— is selected from a straight or branched alkylene, straight or branched alkenylene, straight or branched alkynylene; optionally interrupted by at least one heteroatom;

l is an integer selected from 1-10;

—$C_{(l)}$— is selected from a straight or branched alkylene, straight or branched alkenylene, straight or branched alkynylene; optionally interrupted by at least one heteroatom;

$R_3$ and $R_3$' are each independently selected from C(=O)$R_{20}$, $OR_{21}$, C(=O)$OR_{22}$, $CF_3SO_3$, straight or branched $C_2$-$C_{10}$ alkyl, straight or branched $C_2$-$C_{10}$ alkenyl, straight or branched $C_2$-$C_{10}$ alkynyl;

each of alkyl, alkenyl or alkylnyl groups are optionally substituted by at least one group selected from C(=O)$R_{23}$, $OR_{24}$, halogen, $CF_3SO_3$;

each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, $NH_2$, amine.

In some embodiments, m=1, —$C_{(m)}$— being a C1-alkylene optionally interrupted by at least one heteroatom. In other embodiments, n=1, —$C_{(n)}$— being $C_1$-alkylene, optionally interrupted by at least one heteroatom. In further embodiments, n=2, —$C_{(n)}$— being $C_2$-alkylene, optionally interrupted by at least one heteroatom. In yet other embodiments, n=3, —$C_{(n)}$— being $C_3$-alkylene, optionally interrupted by at least one heteroatom. In other embodiments, l=1, —$C_{(l)}$— is a $C_1$-alkylene, optionally interrupted by at least one heteroatom. In further embodiments, l=2, —$C_{(l)}$— is a $C_2$-alkenylene, optionally interrupted by at least one heteroatom.

In other embodiments, $R_3$ and $R_3$' are each independently selected from $OR_{21}$, straight or branched $C_1$-$C_{10}$ alkyl, straight or branched $C_2$-$C_{10}$ alkenyl, straight or branched $C_2$-$C_{10}$ alkynyl; each of alkenyl or alkylnyl groups are optionally substituted by at least one group selected from C(=O)$R_{23}$, $OR_{24}$, halogen, $CF_3SO_3$; each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, $NH_2$, amine.

In other embodiments, a composition of the invention comprises a compound selected from:

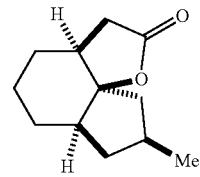

3

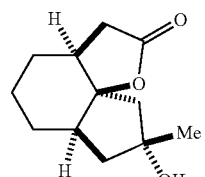

4

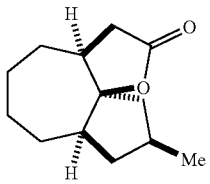

5

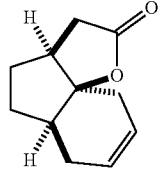

6

The invention further provides a composition as disclosed herein above, for use in the treatment of pain and any related disorder or symptom thereof.

In another aspect the invention provides, a composition as disclosed herein above, for use in the activation (or binding to) of TRPV1 receptor.

In another aspect the invention provides a method of treating pain and pain related disorders and symptoms in a subject in need thereof, said method comprising administering to a patient a composition as disclosed herein above.

The term "pain" as used herein should be understood to relate to any type of pain of any magnitude or duration, caused by any means (internal or external to the human body of a subject treated with a composition of the invention. For example, said pain may be caused by a bodily system whose dysfunction may be causing the pain (e.g., nervous, gastro-intestinal). Said pain can be chronic pain or single episodal pain, having any duration or pattern of occurrence. Said pain may be localaized either in a single or multiple region of the body. Said pain may be of any intensity and time since onset. The pain treated by a composition or compound of the invention may be selected from at least one of the following classifications: nociceptive pain, inflammatory pain (typically associated with tissue damage and the infiltration of immune cells), pathological pain (typically associated with a disease state caused by damage to the nervous system or by its abnormal function such as fibromyalgia, irritable bowel syndrome, tension type headache, etc.).

One of the approaches taken towards pain therapy is the reduction of the hypersensitivity of nociceptors (the peripheral terminals of sensory neurons) by blocking ion channels. One of the options, already in clinical use, is based on the desensitization of pain sensitive neurons, and relies on the activation and internalization of TRPV1. The distinctive example of such agonists is Capsaicin, the pungent active compound of chilly pepper of the genus *Capsicum*, which has been commonly used for the treatment of pain long before the discovery of TRPV1. Studies show that capsaicin induces TRPV1 desensitization, that is, after an initial excessive calcium influx, the receptor becomes unresponsive to subsequent stimuli. Although topical capsaicin is in clinical use, this treatment suffers at the moment from the high "numbers-needed-to-treat" (NNT) because of the low capsaicin concentrations, which are applied to the patients. In addition, for complete desensitization, the treatment needs to be repeated several times. Since the capsaicin application causes a burning pain sensation, local anesthesia is necessary before treatment. Despite this co-treatment, the capsaicin-induced pain only disappears gradually within 1 or 2 days and causes additional discomfort to the patients. Moreover, this treatment needs to be repeated every couple of months. Thus, development of longer-lasting desensitization treatment with a shorter activation phase would enhance the period of analgesia and improve patient compliance. It was previously demonstrated that another naturally found TRPV1 agonist Resiniferatoxin, extracted from the cactus-like plant *Euphorbia resinifera*, produced an efficient depolarizing block.

Unfortunately, access to RTX is limited due to its low natural concentration levels and the synthesis of RTX or its structural derivatives requires a complex multistep approach. Since the first, and the only available, total synthesis of (+)-Resiniferatoxin by Wender in 1997 (44 synthetic steps in total), limited progress has been achieved in synthesizing it for clinical use. Existing routes rely on the preparation of a daphnane rings system and further subsequent functionalization of the scaffold to introduce ortho-ester and the C20-homovanillyl chain. Such transformations, however, require harsh conditions, purification after each synthetic step, and the extensive use of protecting groups. As of 2015, this represents the only complete total synthesis of any member of the daphnane family of molecules. Moreover, remarkable instability of the aqueous solution, make clinical use of RTX impossible. In addition to its exogenous ligands, TRPV1 is also activated by the endogenous lipids, mainly metabolites of Arachidonic acid. The most potent among them is the endocannabinoid N-Arachidonoyldopamine (NADA). This agent, however, cannot be used for pain selective anesthesia due to its effects on Cannabinoid receptor type-1 (CB1)—which mediates widespread effects.

Thus, in one aspect of the present invention the inventors have found that the compounds of the present application being tricyclic spiranoid lactones could provide an analgesic effect by binding to the TRPV1 receptor.

The term "treatment" as used herein refers to the administering of a therapeutic amount of a composition of the present invention comprising a compound of the present invention, which is effective to reduce, prevent or ameliorate undesired symptoms associated with the sensation of pain caused by any means (internal or external to the human body of a subject in need thereof).

The "effective amount" for purposes disclosed herein is determined by such considerations as may be known in the art. The amount must be effective to achieve the desired therapeutic effect as described above, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

The pharmaceutical compositions of the invention may comprise additionally any other suitable substances such as other therapeutically useful substances, diagnostically useful substances, pharmaceutically acceptable carriers or the like.

When referring to "composition(s)" or "pharmaceutical composition(s)" the present invention seeks to include any compositions suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents. Pharmaceutical compositions suitable for oral administration may be presented as discrete dosage units such as pills, tablets, dragdes or capsules, or as a powder or granules, or as a solution or suspension. The active ingredient may also be presented as a bolus or paste. The compositions can further be processed into a suppository or enema for rectal administration. The invention further includes a pharmaceutical composition, as hereinbefore described, in combination with packaging material, including instructions for the use of the composition for a use as hereinbefore described. For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated.

Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any integer or step or group of integers and steps.

BRIEF DESCRIPTION OF THE FIGURES

In order to better understand the subject matter that is disclosed herein and to exemplify how it may be carried out in practice, embodiments will now be described, by way of non-limiting example only, with reference to the accompanying figures, in which.

DETAILED DESCRIPTION OF EMBODIMENTS

There is remarkable overlap in the structures of the above-mentioned natural products. It was found by the inventor of the preset application that most of the tricyclic spiranoid lactones, such as Alliacanes, Arteannuins, Allamancins, Teucrolins, and many others, are derived from a simple precursor via controlled intramolecular cascade transformations.

Figure 2:
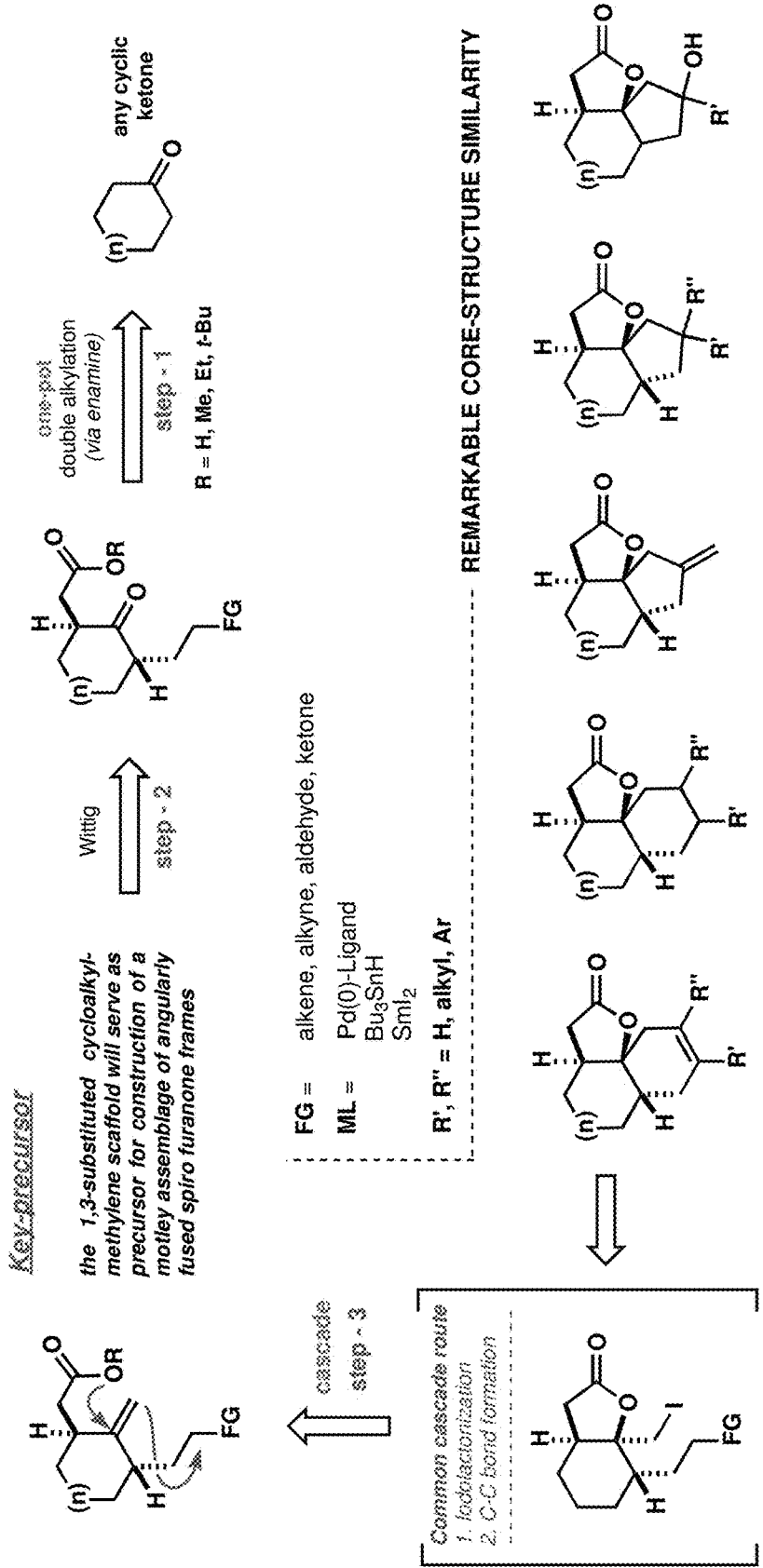
FIG. 2. Illustrates the 3-step strategy and structural similarity between families.

At the outset, the 1,3-substituted cycloalkylmethylene scaffold, which can be obtained in two steps from a simple cyclic ketone, and can serve as an operationally acceptable key-precursor for the construction of tricyclic spiranoid lactones (FIG. 2). The retro-synthetic analysis was cognizant of this framework and hypothesized that the desired tricyclic systems is successfully constructed through simple and straightforward cascade cyclizations. It is noteworthy to point out that although the structures of spiranoid lactones are closely related, no attempt has been reported to date to synthesize all of the structures using a shared and common synthetic sequence.

On the basis of remarkable core-structure similarities between the above-mentioned products, the inventor has elaborate upon the novel concept for developing a rapid and practical synthesis strategy of complex functionalized natural and never before-observed frames. The inventor has developed a general and common diversity-oriented synthesis of phylogenetically and structurally different tricyclic angularly fused systems via controlled and regioselective cyclizations of a simple key-precursor (FIG. 2). This novel synthetic strategy is short, regioselective, and offers the possibility to access a broad spectrum of quaternary carbon-centered oxa-spiro based structures.

A readily accessible key molecule that is of lesser complexity than the target natural products was elaborated by simple synthetic sequences. This yielded a motley assemblage of spiranoid lactones of varying complexity containing a similar pharmacophore (as may be clearly observed in FIG. 2).

Only a few of the naturally occurring combinations for angularly fused tricyclic scaffolds are known to exist: 5-5-5, 6-5-5, 6-5-6, and 6-6-6 (other combinations are extremely rare).

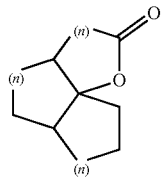

(n) = 1 and 2 are the most common naturally accuring combinations

The present invention's methodology enables the production on new variations of angularly fused structures (i.e., scaffolds containing 7-, 8-, 9-, or macro-membered rings), which provides access to a new range of compounds that have never-before been available and observed. These compounds closely resemble common natural products and carry enormous potential for becoming valuable drugs/therapeutic agents.

The present invention provides simple key precursors for the synthesis of structurally related, angularly fused tricyclic spiranoid lactones and natural products of various families, such as for example Arteannuins, Alliacanes, Allamancins, and others.

Furthermore the invention provides a general and universal protocol for the rapid synthesis of desired scaffolds in order to overcome some of the key limitations of stepwise synthesis, specifically the requirement for a long reaction time, chromatography, and protecting group manipulations. The inventors have designed methodology to synthesize representative molecules of families of natural products and never before observed scaffolds.

Figure 3:
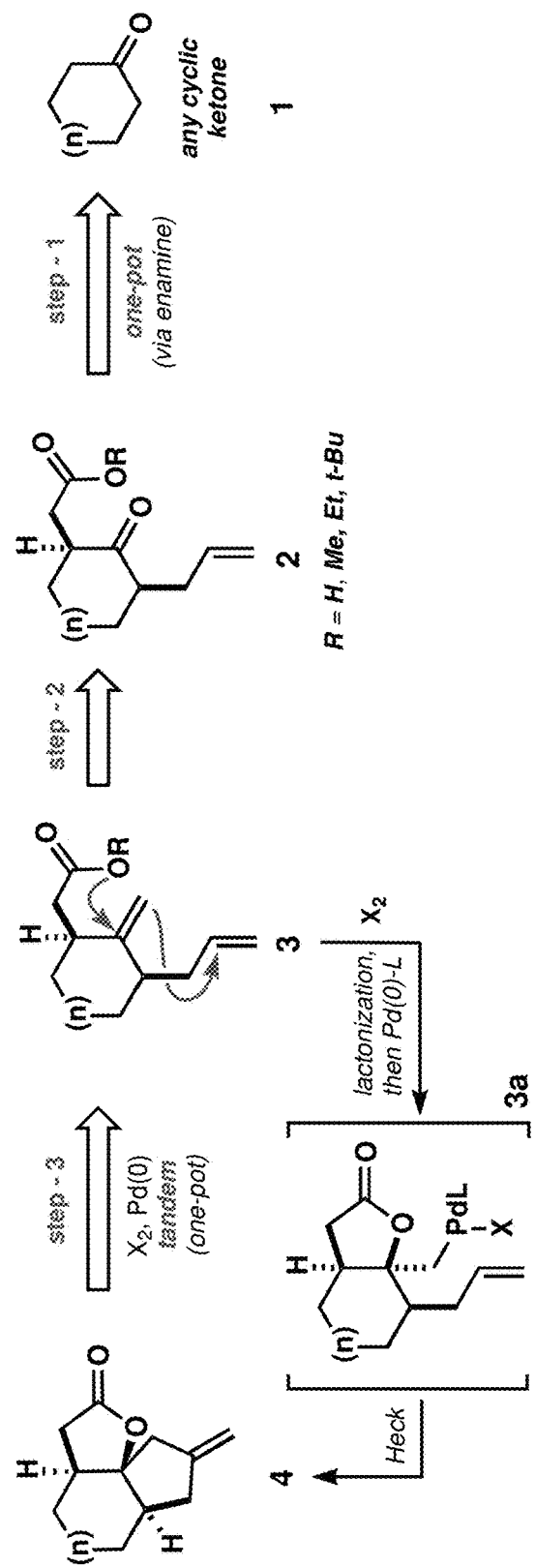
FIG. 3. Illustrates the three-step synthesis of tricyclic methylene-spirofuranones via $X_2$/Pd-L catalyzed cascade cyclization.

Direct Synthesis of Methylene-Spiranoid Lactones:

FIG. 3 shows a three-step synthesis of methylene-spiranoid lactones. A rapid synthesis of the key-precursor (3) and its further application in cascade $I_2$/Pd(0)L-mediated cyclizations to obtain the desired frame. Such a reaction provides a powerful disconnection for complex tricyclic angularly fused methylene-furanones.

1) Synthesis of key-precursor: In general, the key-precursor (3) (FIG. 3) might be accessible through the sequence of two synthetic steps from any cyclic ketone as demonstrated in FIG. 3.

First, the di-armed intermediate (2) is prepared through the double enamine α-alkylation of cyclic ketone (1) with methyl/ethyl/or t-Bu-bromoacetate ("1$^{st}$ arm") and allylbromide ("2$^{nd}$ arm"). Isolated compound 2 will then undergo Wittig methylenation (ester group is stable under such conditions) to yield the desired key-precursor 3. The enamines of cyclopentanone, cyclohexanone, cycloheptanonone, and cyclooctanone were selected as the starting materials. This tandem one-pot double α-alkylation of cyclic ketones via an enamine intermediate is dependent on the base employed.

Reaction conditions: a) allylbromide (0.8 equiv), enamine (1.0 equiv), MeCN, r.t. 2 h; b) t-Bu-2-bromoacetate (1.0 equiv), DIEA (1.0 equiv), MeCN, 50° C.; c) KOt-Bu (2.0 equiv), MePPh$_3$Br (2.0 equiv), THF.

Figure 4:
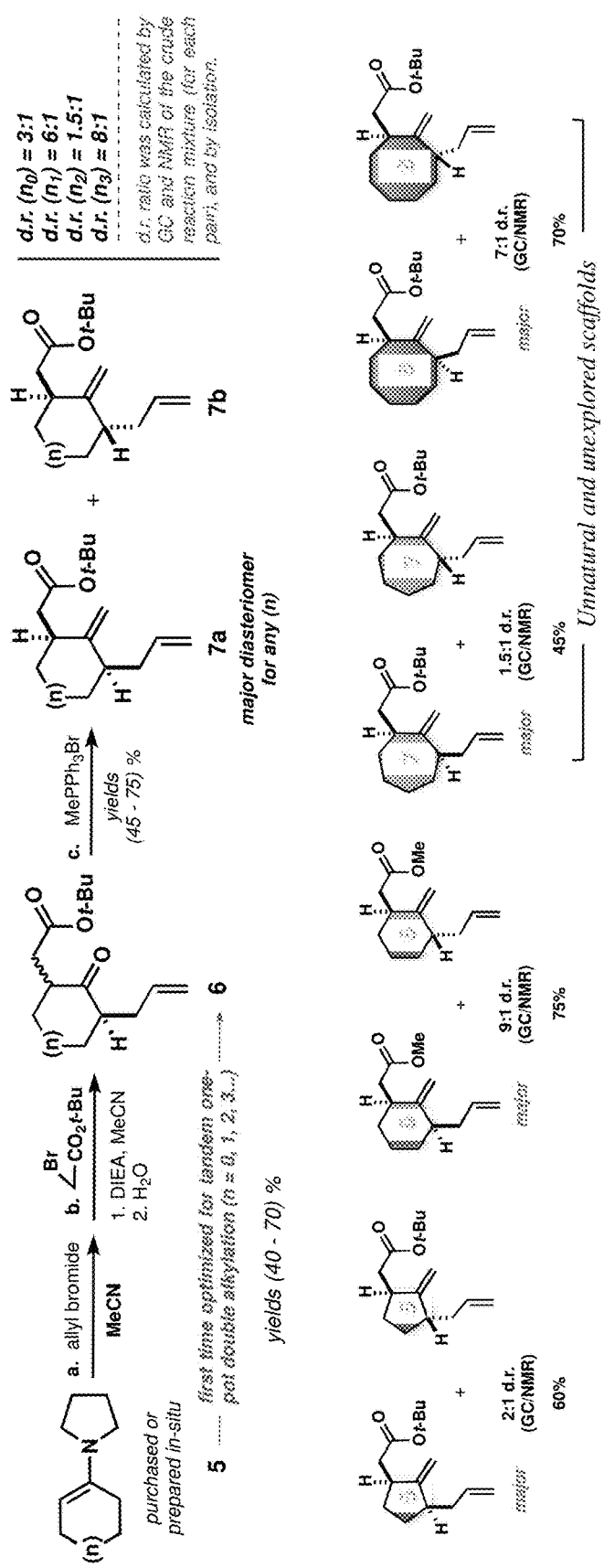
FIG. 4. Illustrates the synthesis of the key precursors for cascade cyclizations.

A variety of bases were examined, for example DIEA (Hunig's base) was found to be highly effective for this reaction forming an intermediate (6): the first alkylation of an enamine was followed by addition of DIEA and t-Bu-bromoacetate in one-pot (see FIG. 4 for detailed reaction conditions). Further Wittig methylenation of isolated intermediate 6 generated precursors 7a and 7b in high yield. The diastereomeric product ratio is dependent on the size of a ketone ring. The d.r. was calculated by GC and NMR of the crude reaction mixture (for each pair), and finally by isolation. It should be noted that both diastereomers are clearly separated on column chromatography.

Figure 5:
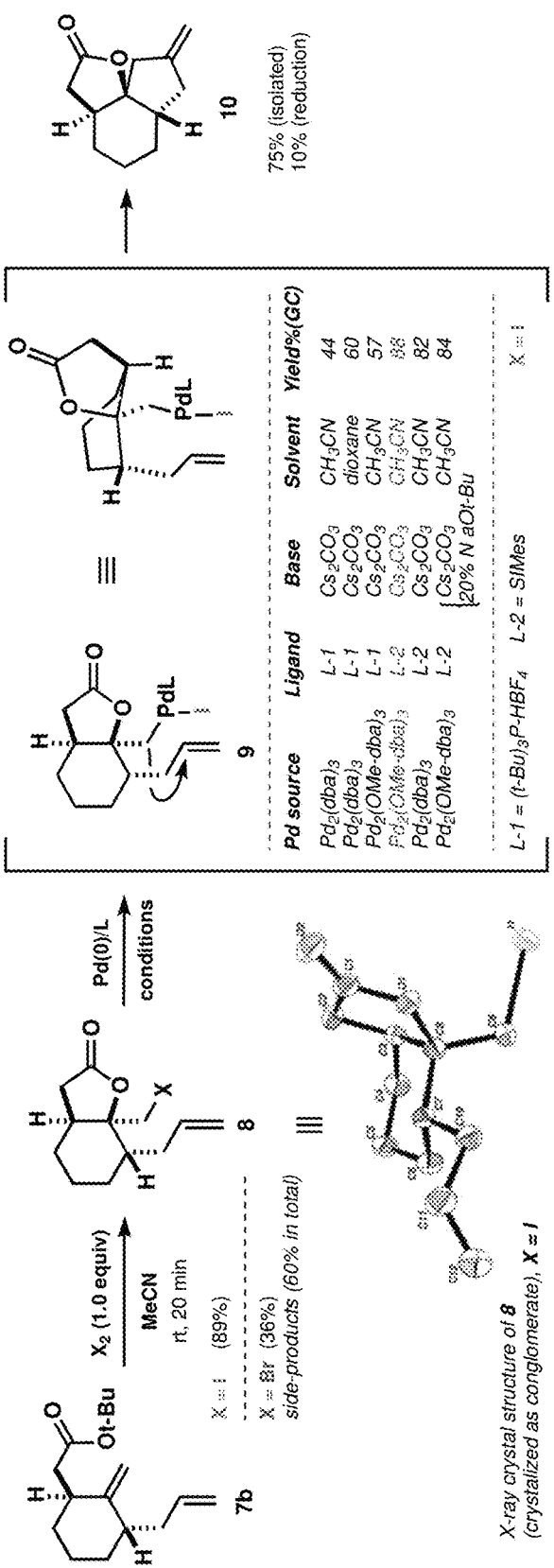
FIG. 5. Illustrates the stepwise approach: optimizations for lactonization and cyclization (Heck-type C—C bond formation).

2) Stepwise cyclizations: The present invention's strategy is based on the notion that, in the presence of $I_2$ and Pd-Ligand catalyst, the key precursor 3 (FIG. 3) generates a lactone ring (directly from ester; no hydrolysis is required), and further undergoes an intramolecular cyclization to form the corresponding tricyclic lactone 4 in one step (Pd-mediated transformations are among the most studied processes for C—C bond formation). Both transformations are impressive in terms of simplicity and the substrates. FIG. 5 demonstrates the stepwise approach towards the rapid synthesis of methylene-furanone 10.

In one example, 5-exo halo-lactonization of 7b (in the presence of Br$_2$, I$_2$ or ICl) occurred selectively in a cis-fashion generating pure lactone 8, which was followed by Pd(0)/L-catalyzed carbon-carbon bond formation via an alkylpalladium intermediate 9. This was analogous to the intramolecular Heck reactions of unactivated alkyl halides. The single diastereomer 10 was than obtained in 75% isolated yield. Crystallographic evidence: The solid iodolactone 8 was isolated (crystalized as a conglomerate), and the structure was confirmed by NMR and X-ray. In comparison with the best Pd/ligand/base/solvent system found for the desired alkyl-Heck reaction [Pd$_2$(OMe-dba)$_3$/SIMes/Cs$_2$CO$_3$/acetonitrile; entry highlighted in blue], other combinations were less effective.

A similar synthetic sequence was used to prepare the diastereomeric mixture of iodolactones. In this case, the reaction was carried out under the optimized conditions in the presence of non-separated diastereomeric key precursors 7a and 7b (n=1). Both lactones are clearly separated by column chromatography and maintain the same d.r. as the starting precursors (d.r 6:1, FIG. 4). One important finding is that the diastereomeric product ratio might be tuned. The use of methyl-ester provided a higher d.r. (9:1) and allowed for another convenient protocol to be developed.

Figure 6:
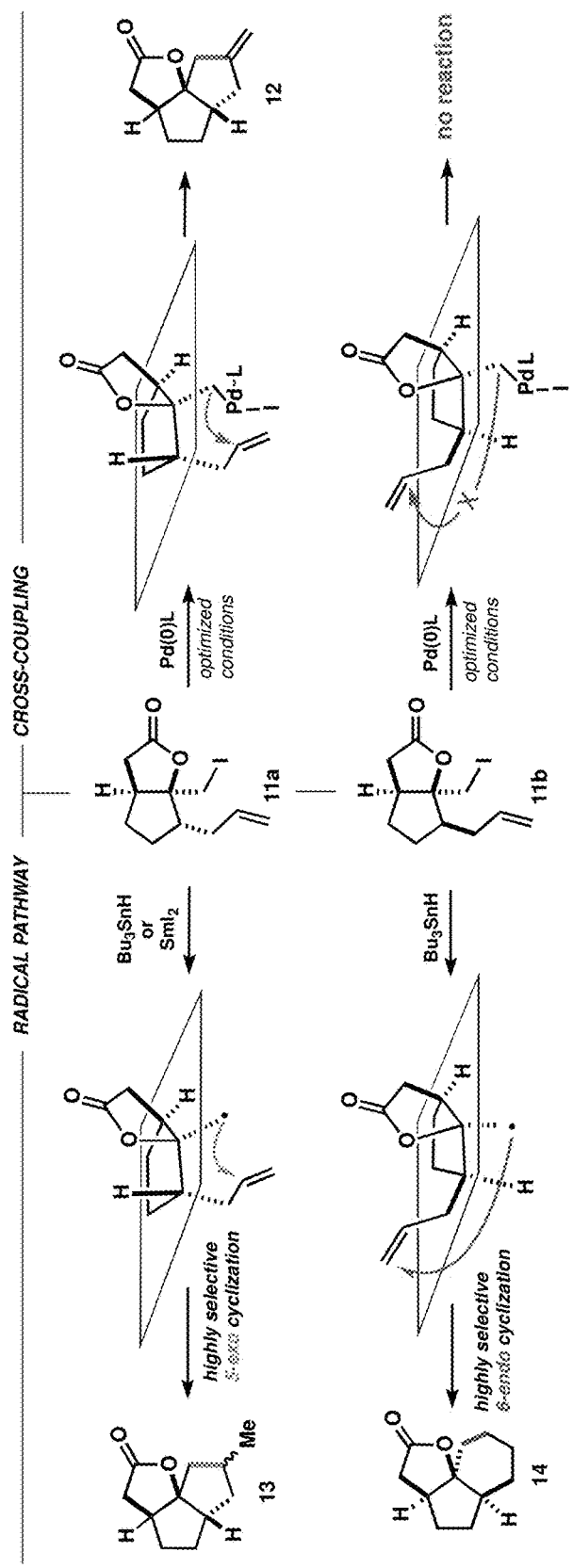
FIG. 6. Illustrates the substrate-controlled regioselective cyclization of fused iodolactones.

3) Selectivity and Mechanistic insight: To demonstrate the utility of the described tandem process for double cyclizations and the creation of naturally occurring molecular architectures, another precursor with a five-membered ring topology was targeted using optimized conditions: The key-precursor 11a was prepared (separated from 11b) and combined with the Pd(0)-SIMes catalyst to generate the single tricyclic diastereomer 12 as detailed in FIG. 6 (the cross-coupling route). In contrast, the diastereomeric precursor 11b did not undergo an expected 5-exo cyclization under any set of conditions.

Without being bound by theory, such an unusual and rare substrate-controlled regioselective behavior might be due to the geometric difference between cis- and trans-fused iodolactones (the distance between Pd/L complex and the alkene group).

The iodolactones 11a and 11b are significantly different in activity, the inventors have subjected both diastereomers to radical coupling conditions in the presence of Bu$_3$SnH or SmI$_2$, showing that reactions that proceeded through highly regioselective pathways generate 5-exo (13) or 6-endo (14) products (FIG. 6) exclusively. Differences in activity result from geometric variations between the two scaffolds.

The observed transformations (exclusively associated with tricyclic pentanoic systems) are highly selective and controlled by the substrate's architecture. This is the first case of intramolecular $SmI_2$-mediated coupling of alkyl iodide with unactivated alkenes.

4) The cascade cyclizations (limitations and proposed solutions): As can be understood from the described transformations, both cyclizations are initiated by iodolactonization and followed by C—C coupling reaction.

The desired rapid synthesis of spiranoid lactones is accomplished by executing the following operation: a reaction of key precursors is initiated through the addition of ICl or $I_2$ (stirred at r.t. under inert atmosphere), followed by a mixture of a "quencher", catalyst, and base (the Pd/L/base mixture will be prepared in separate vials and injected directly into the precursor flask). Such a pathway offers the opportunity to probe the ability of this cascade cyclization approach to overcome the barriers associated with stepwise pathway, which requires isolation and purification of intermediates after each synthetic step.

5) Scaffold modifications, robustness, and other applicability of the novel platform: Common reaction conditions were identified for anchoring other "arms" of a central ring through the quaternary spiro-center, thus transforming the resulting key precursors into the corresponding tricyclic spiranoid lactones. Other substituents were introduced into the cyclohexylmethylene scaffold and a wide range of precursors were found with varying substitution patterns (various "arms") can be converted into the tricyclic targets sharing the same common protocol: 1) double alkylation, 2) olefination, and 3) cascade cyclization. The cyclization conditions using this methodology that affects the $I_2$/M-L mediated cascade reactions with a broad variety of substrate combinations was developed. This process determines the optimal means for effecting the adherence of different block combinations ("arms") as a way of selecting the best catalyst and reaction conditions.

Synthesis of Hydroxy-Spirofuranones Via the $I_2/SmI_2$ Cascade Cyclization

Figure 7:
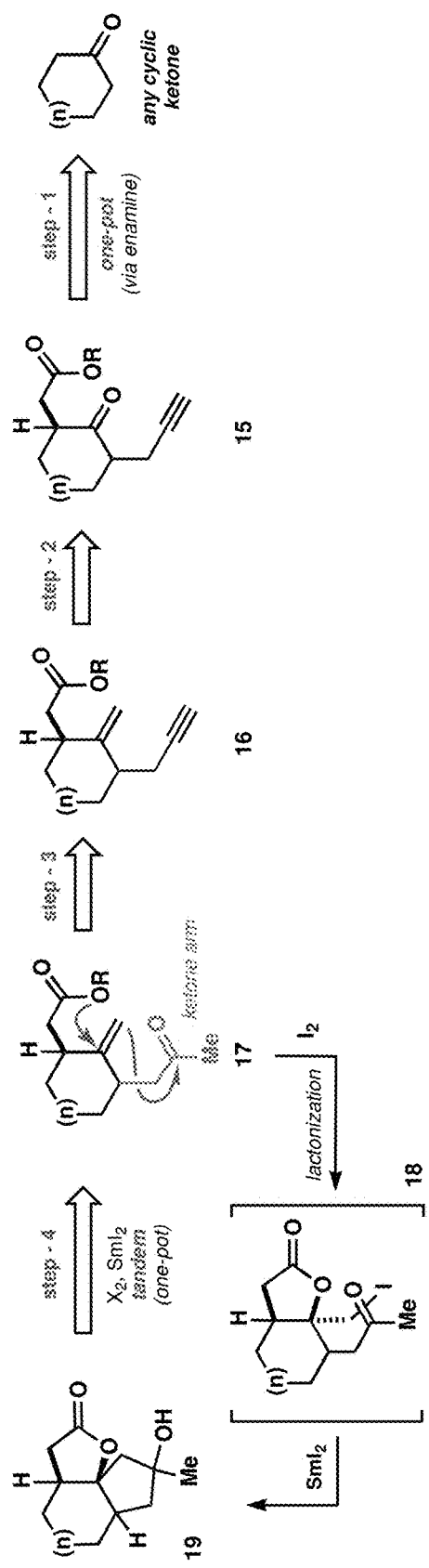
FIG. 7. Illustrates the general retro-synthetic perspective: 4-step synthesis of hydroxy-spirofuranone.

The ketone-arm modified key precursor 17 (FIG. 7) in this example provides innovative and efficient access to another tricyclic scaffold 19: the hydroxy-spirofuranone (the ketone group is introduced into the main core via the propyne blocks 15 and 16, as shown on the Figure).

The synthetic scaffold shows a high degree of analogy to the previously mentioned precursor 3 and might be generated through the sequence of three synthetic steps from any cyclic ketone. The sequence involved ring closures of the precursor via tandem cyclizations as in the example previously described.

Reaction conditions: a) 3-bromopropyne (0.5 equiv), enamine (1.0 equiv), MeCN, r.t. 2 h; b) t-Bu-2-bromoacetate (1.0 equiv), DIEA (1.0 equiv), MeCN, 50° C.; c) KOt-Bu (2.0 equiv), MePPh$_3$Br (2.0 equiv), THF; d) HgO (0.2 equiv), $H_2SO_4$ (4%), MeOH, r.t. 1 h.

Figure 8:
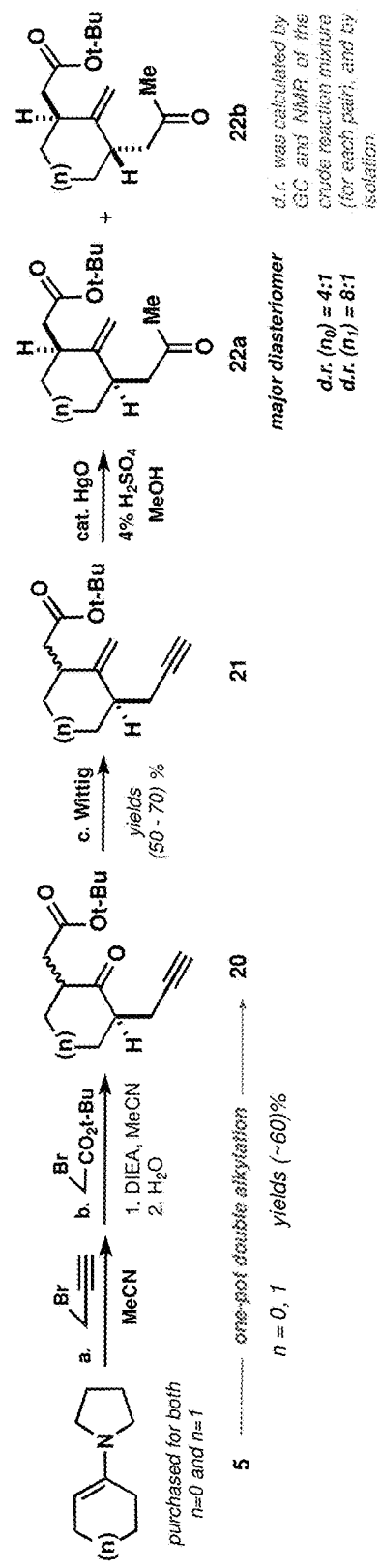
FIG. 8. Illustrates the synthesis of the key precursors for cascade cyclizations.
Figure 9:
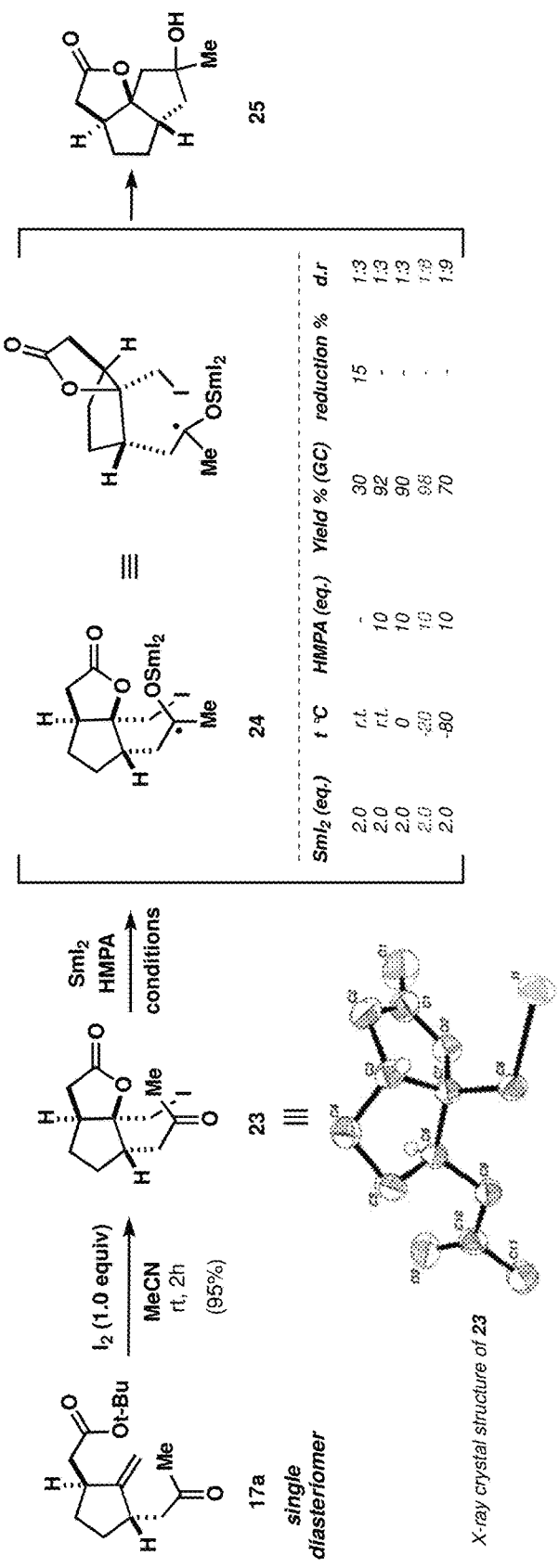
FIG. 9. Illustrates the stepwise approach: optimization for lactonization and $SmI_2$-mediated cyclization.

The addition of $I_2$ facilitates the formation of iodolactone, which was then subjected to cyclization-hydroxylation conditions in the presence of $SmI_2$ and HMPA for the desired hydroxy-spirofu ranones. A representative set of reactions that have already been performed is shown on FIGS. 7-9.

Figure 10:
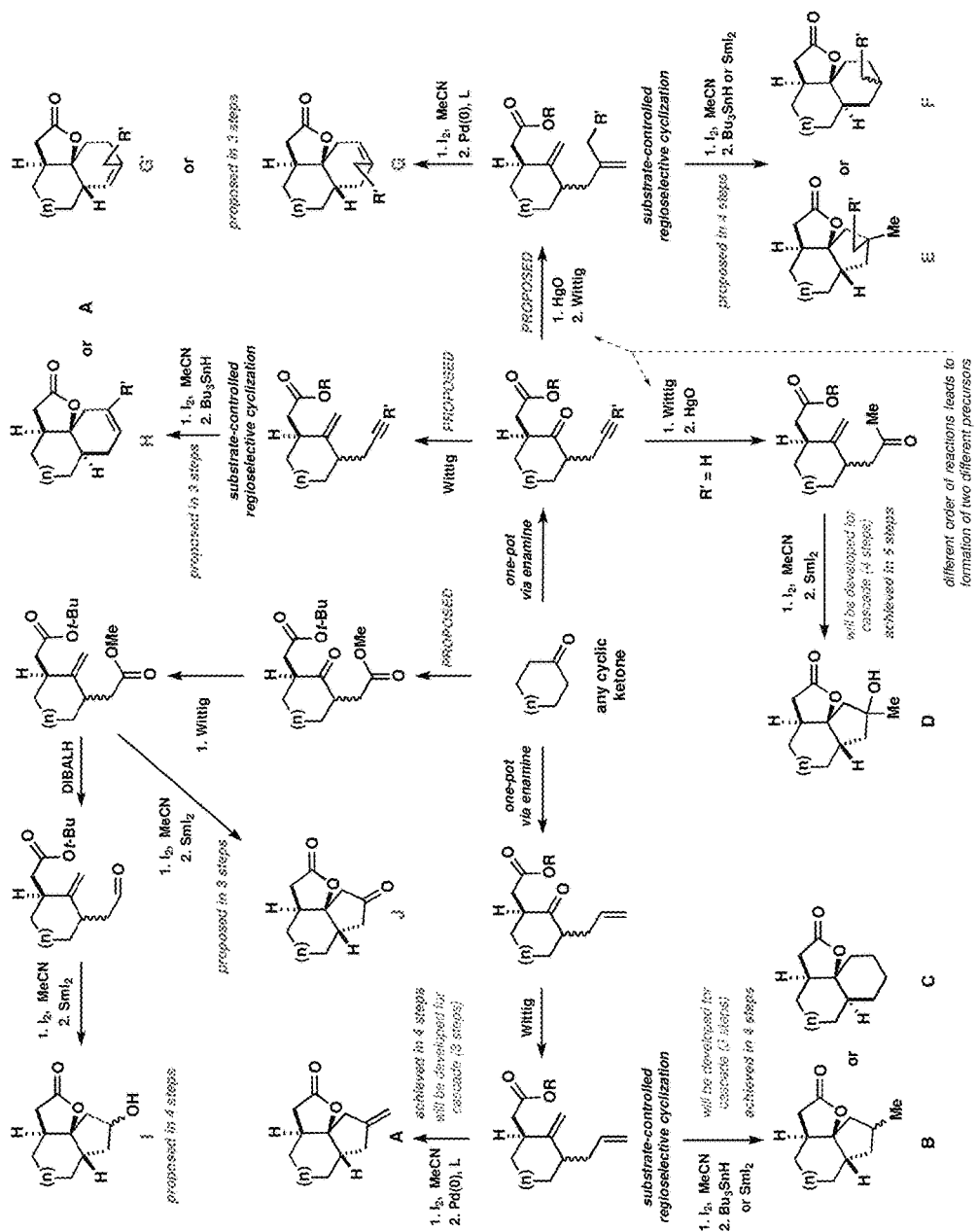
FIG. 10. Illustrates the rapid and practical synthesis of spiranoid lactones.

Collective Synthesis of Spiranoid Lactones:

Using the building blocks designed and the general reaction conditions in hand allows for the preparation of most of the tricyclic scaffolds of angularly-fused spiranoid lactones found in nature, as well as never-before-seen architectures. Linear key precursors can be used to yield tricyclic scaffolds E, F, G, H, I and J (and their structural analogues) in just 3-4 steps through simple synthetic sequences (FIG. 10). It should be noted that the entire synthetic route could be accomplished without the need for protecting groups and with most reactions being performed under moderate conditions.

1) Spiranoid lactones E and F: Introduction of an additional alkene substituent into the cycloalkylmethylene scaffold is performed by reversing the order of methylenation and oxymercuration reactions, thus generating novel precursor 26. Under Bu$_3$SnH or $SmI_2$ conditions the modified key precursor 26 undergoes regioselective ring closure, which creates two novel types of tricyclic lactones E and F (FIG. 10). Both transformations are carried out under the regioselective control.

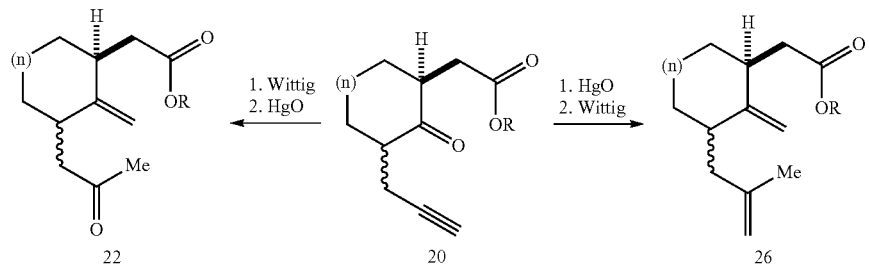

already demonstrated in "preliminary data" section

The figure reflects a single diastereo-pattern, while both diastereomers i and ii formed and are expected to be easily separated:

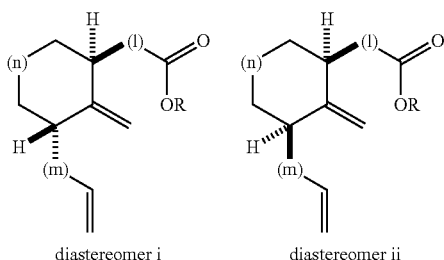

diastereomer i    diastereomer ii

System potential, functionality and robustness:

-rings size variability
-stereo control
-early-step prediction and design of rings functionality
-easy post-modifications of the designed frames:
  alkylation, epoxidation, etc.
-each transformation is optimized for stepwise synthesis
  (every interemediate might be separated)

Figure 11:
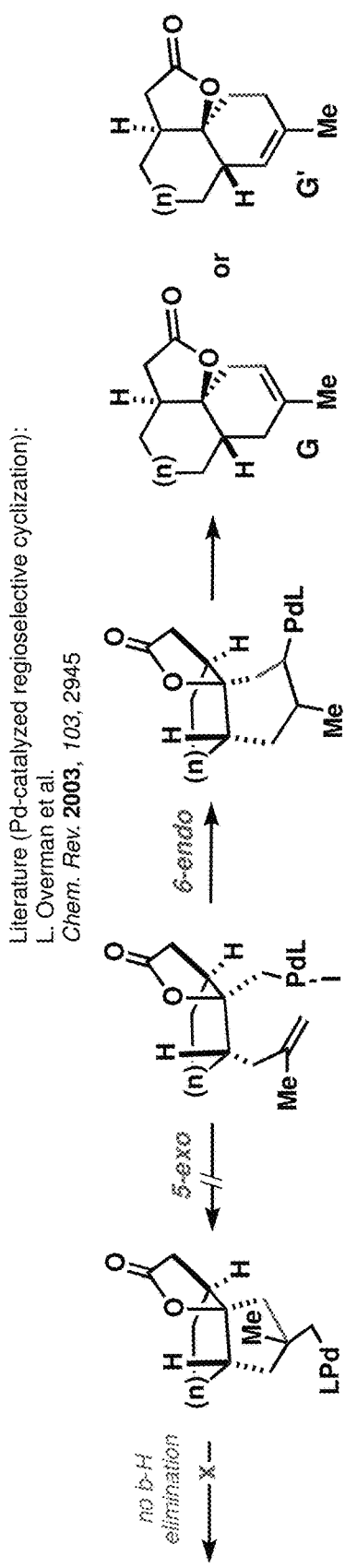
FIG. 11. Illustrates the rapid and practical synthesis of spiranoid lactones (proposed selectivity).

2) Spiranoid lactones G and G': Construction of compounds G and G' is another element in the figure. The selective regioselective generation of the 6-endo isomer is carried out under Pd(0)L conditions as shown in FIG. 11. No 5-exo termination takes place in the proposed sequence.

Figure 12:
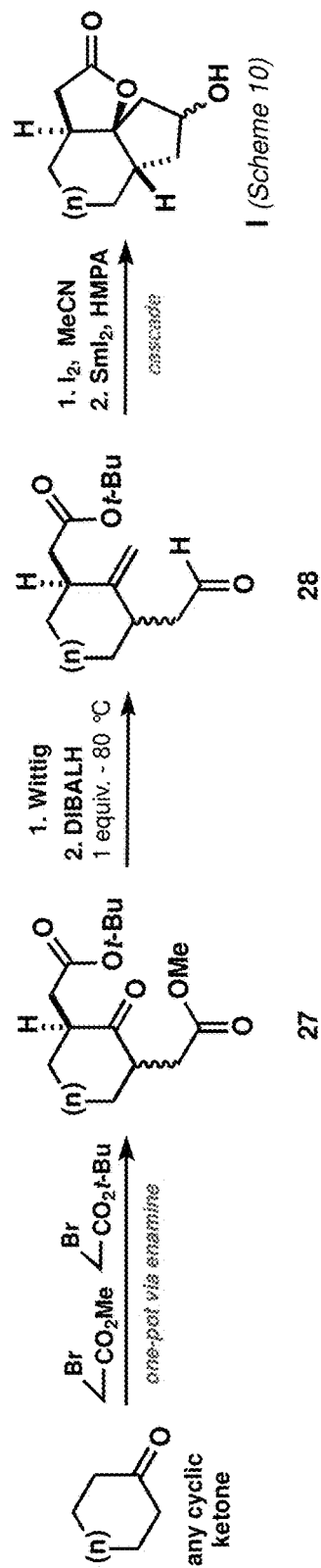
FIG. 12. Illustrates the synthesis of hydroxy-spiranoid lactones.
Figure 13:
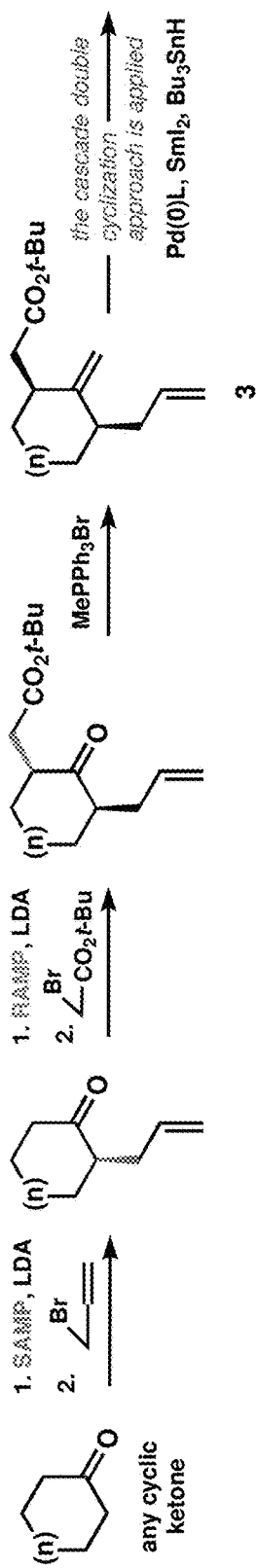
FIG. 13. Illustrates the enantiospecific synthesis of key precursor 3.

3) Hydroxy-spiranoid lactone I: Based on the described approach for synthesis of tricyclic system D, we envision that hydroxy-spiranoid lactones of type I (FIG. 10) may also be generated through a similar short synthetic sequence via cascade cyclization of the key-precursor 28 (FIG. 12). Such a precursor could be obtained through methylenation and hydrolysis of an easily accessible diester-intermediate 27, followed by selective DIBALH-mediated reduction of the methyl-ester (FIGS. 10 and 12).

4) Spiranoid lactone H: Having established a modular 3-4 step sequence for the assembly of tricyclic scaffolds A-G, and I from components of similar synthetic complexity, we will demonstrate the versatility of the methodology for the synthesis of analogue H. The easily accessibly intermediate 20 (FIG. 8) will undergo methylenation and will be further subjected to $Bu_3SnH$ conditions, thus generating two frames: H and A (FIG. 10). Factors controlling the proposed selectivity will be investigated.

Thus, the present invention provides a model for the highly efficient preparation of spiranoid lactone scaffolds. The single precursor can be selectively converted to form all of the described products by the controlled intramolecular cyclizations.

Application of Methodology to Enantiospecific Synthesis of Tricyclic Spiranoid Lactones:

The enantiospecific pathway for the synthesis of described scaffolds might be easily designed through the Corey-Enders RAMP/SAMP hydrazone alkylation of cyclic ketone with an appropriate "arm" chain.

Isolated compounds undergo Wittig olefination to generate the desire enantiopure key precursors. This strategy can be applied to any cyclic ketone and thus represents a streamlined and highly versatile solution for constructing a variety of natural and never-before-seen scaffolds. Below is an example of the proposed concept.

Figure 1:
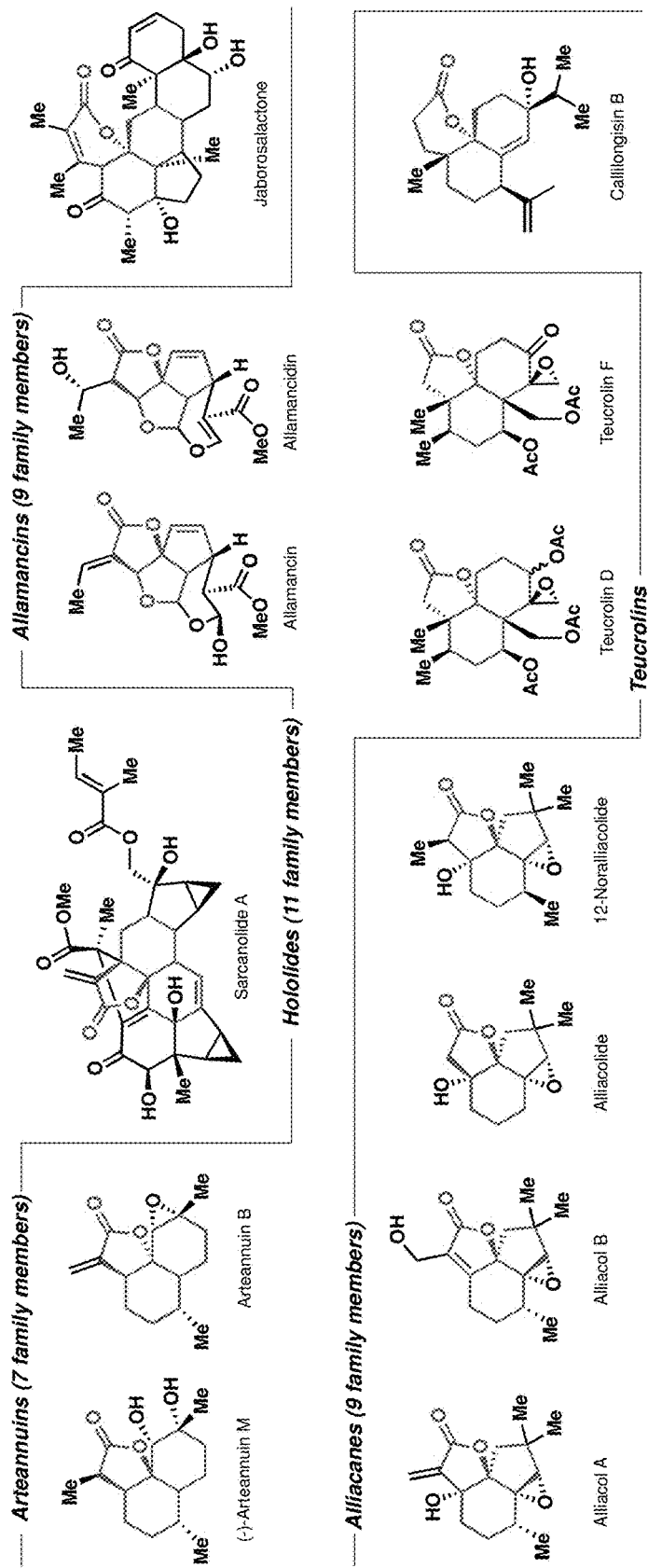
FIG. 1. Illustrates the natural products from diverse biological origins that share the oxaspirofuranone ring systems.

Application of Methodology to the Total Synthesis of Natural Products:

The broad applicability and potential of the described platform of the invention allows utilization to complete total syntheses of a series of tricyclic angularly-fused natural products using the same retrosynthetic algorithm, collection of very similar building blocks, and common reaction conditions. Application of this approach only requires preparation of the corresponding capping elements. For example, the methodology of the present invention is suited to accomplish the total synthesis of Alliacanes (FIG. 1). It is noteworthy to point out that although the structures of alliacols A, B, and Alliacolide are closely related, the synthesis of all three natural products using a shared synthetic sequence has not been reported to date.

In the retrosynthetic analysis, a common key precursor needs to be devised. This precursor resembles the starting material of the cascade cyclization required for the construction of the signature structure element 36 of alliacanes.

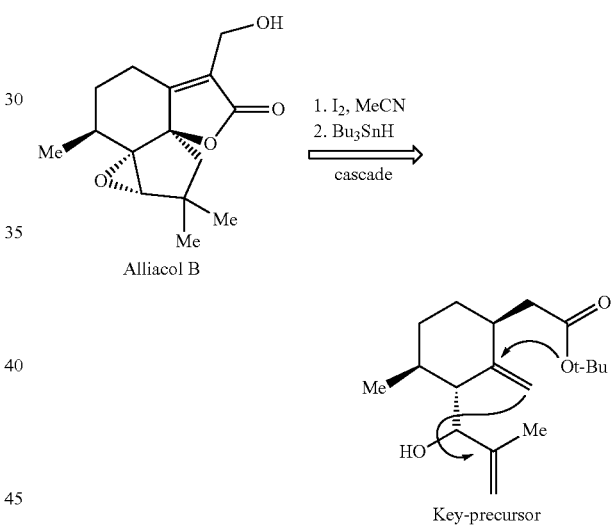

Figure 14:
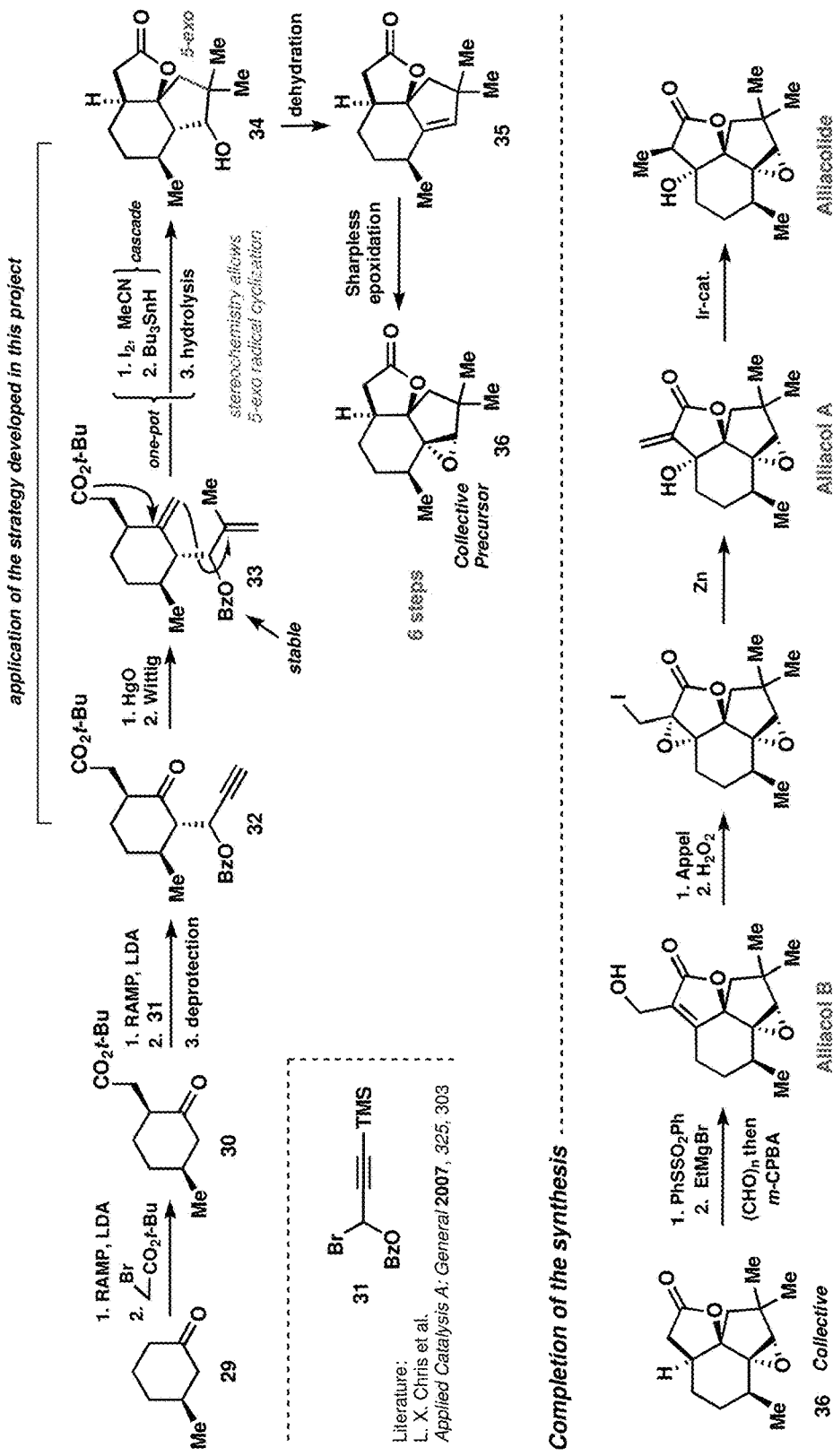
FIG. 14. Illustrates the synthesis of collective key precursors and construction of Alliacanes: Alliacol A, B, and Alliacolide.
Figure 15:
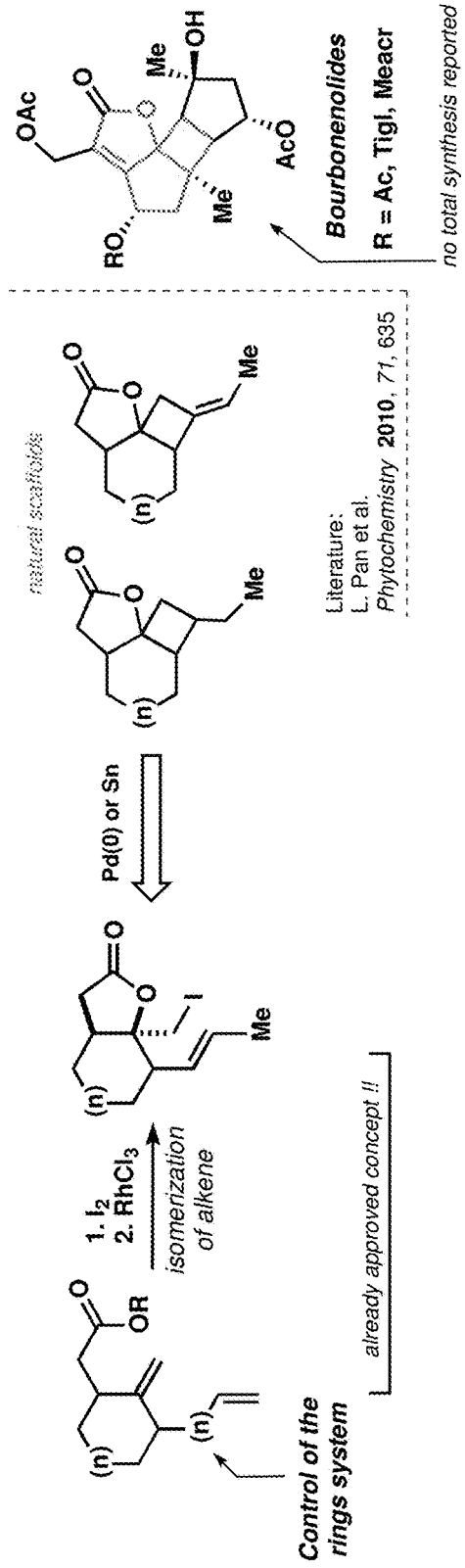
FIG. 15. Illustrates some applications of novel strategy.

FIG. 14 details the proposed reaction pathway for the construction of the signature structure element (from precursor 33) and its further application in the continuous synthesis of all of the desired natural products.

The methodology of the present application allows for rapid access (3-4 steps) to a mixture of easily separable diastereomers through a precursor, lactone or products stages. The produced compounds have potential therapeutic activity. As demonstrated above, the methodology of the invention is highly versatile and allows construction of numerous combinations of angularly fused tricyclic systems.

The following figure visualizes the enormous capabilities of the methodology of the invention originating from a single core substrate (precursor 3 is demonstrated as one example out of many possible primary scaffolds) and yielding an abundance of modified products that are all generated using simple, key transformations that are outlined in this proposal.

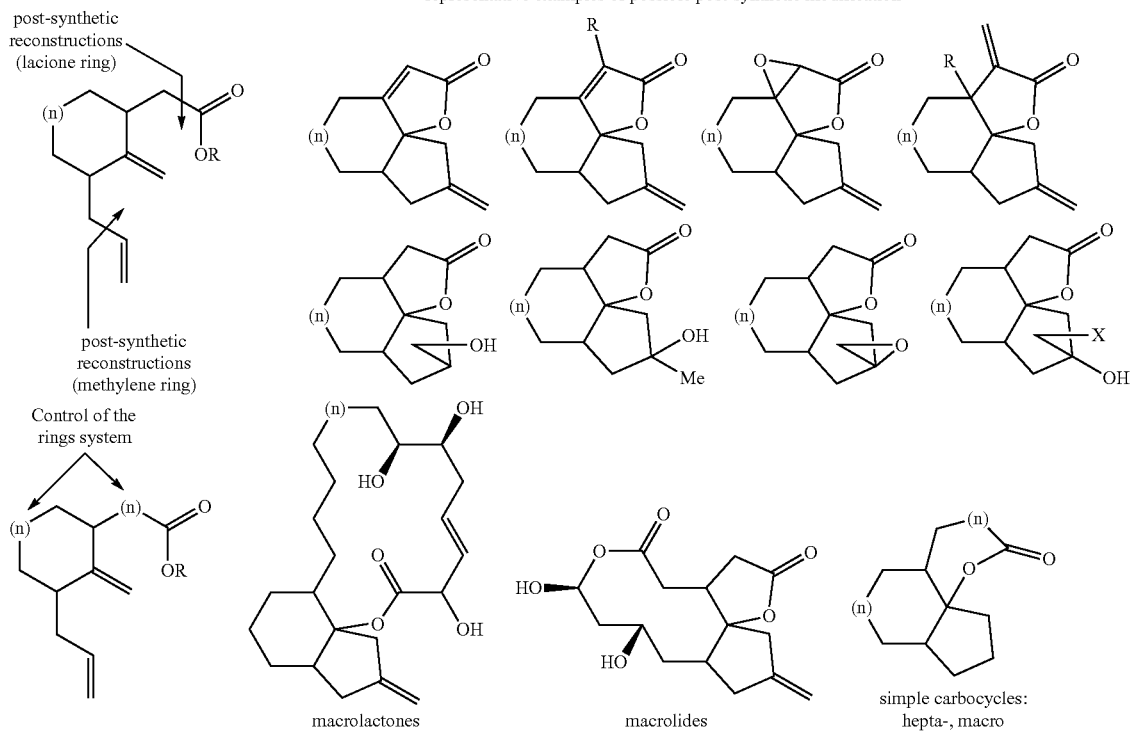

representative examples of possible post-synthetic modification

Precursor 3 is demonstrated as one example out of many possible primary scaffolds

Experimental Data

Unless otherwise stated, all reagents were purchased from commercial suppliers and used without further purification. Solvents used in the reactions were distilled from appropriate drying agents prior to use. Reactions were monitored by thin-layer chromatography (TLC) on silica gel 60 F254 aluminium plates (Merck) and/or gas chromatography-mass spectrometry (GCMS). Visualization of compounds on TLC was accomplished by irradiation with UV light at 254 nm and/or vanillin stain. GCMS Analysis was performed with 'Agilent 7820A' gas chromatograph equipped with 'Agilent 5975' quadrupole mass selective detector, using a Agilent HP-5MS capillary column (30 m, 0.25 mm, 0.25 μm film). Column chromatography was performed using silica gel 60 (particle size 0.040-0.063 mm) purchased from Sigma-Aldrich. Proton and carbon NMR spectra were recorded on Varian Mercury 300 MHz or Varian Mercury 500 MHz spectrometer in deuterated solvent. Proton chemical shifts are reported in ppm (δ) relative to tetramethylsilane with the solvent resonance employed as the internal standard (CDCl$_3$, δ 7.26 ppm). $^{13}$C chemical shifts are reported in ppm from tetramethylsilane with the solvent resonance as the internal standard (CDCl$_3$, δ 77.0 ppm). Data are reported as follows: chemical shift, multiplicity (s=singlet, d=doublet, t=triplet, q=quartet, m=multiplet), integration and coupling constants (Hz). High resolution mass spectra were determined on a Thermo Scientific LTQ Orbitrap XL (FTMS). Infrared (IR) spectra were recorded on a ThermoFischer Scientific NICOLET iS10 spectrometer. Abbreviations: pTSA (p-Toluenesulfonic acid), THF (tetrahydrofuran), DIEA (N,N-Diisopropylethylamine) dr (diastereomeric ratio), SIMes-HBF$_4$ (1,3-Bis(2,4,6-Trimethylphenyl)-4,5-Dihydroimidazolium Tetrafluoroborate), HMPA (hexamethylphosphoramide), AIBN (Azobisisobutyronitrile), DBU (1,8-Diazabicyclo[5.4.0]undec-7-ene).

1. Synthesis of Precursors

General Procedure A: One-Pot α,α'-Dialkylation of Enamines of Cyclic Ketones

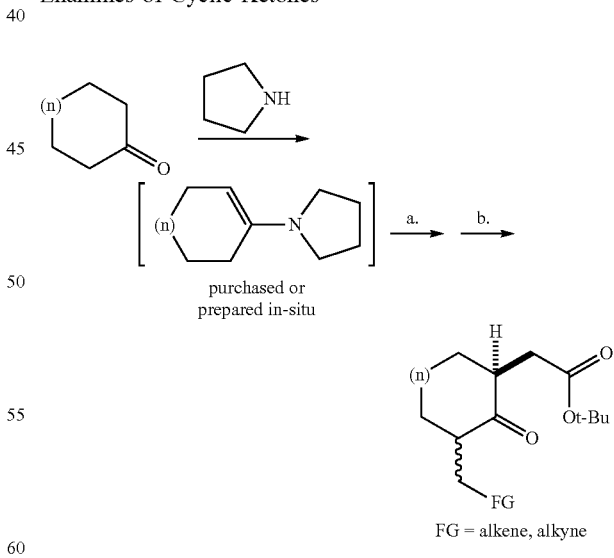

1-(cyclopent-1-en-1-yl)pyrrolidine, 1-(cyclohept-1-en-1-yl)pyrrolidine, 1-(cyclooct-1-en-1-yl)pyrrolidine were freshly prepared by refluxing the corresponding cyclic ketone (1.0 equiv) and pyrrolidine (3.0 equiv) in dry toluene (1 M), in the presence of catalytic amount of pTSA, till all water was distilled by Dean-Stark apparatus. After removal of toluene and traces of pyrrolidine by vacuum evaporation the crude compound was used directly.

a. Unsaturated alkyl halide was added dropwise to a 1 M solution of enamine of corresponding ketone in dry MeCN. The reaction mixture was stirred for 1 h at room temperature;

b. DIEA was added as one portion, followed by slow addition of tert-butyl 2-bromoacetate. The mixture was refluxed for 12 h, then quenched with water and refluxed for further 1 h.

After cooling to room temperature, the solution was diluted with diethyl ether and the aqueous layer was extracted with diethyl ether. The combined organic layers were washed with brine, dried ($Na_2SO_4$), filtered and concentrated in vacuo. The product was purified by flash chromatography (silica gel, hexane/ethyl acetate) to yield the α,α'-dialkylated cyclic ketone.

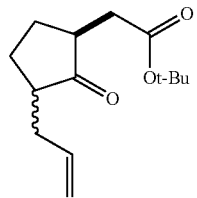 [SMILES: C=CCC1CC[C@@H](CC(=O)OC(C)(C)C)C1=O]

tert-butyl 2-(3-allyl-2-oxocyclopentyl)acetate: General procedure A was applied using freshly prepared 1-(cyclopent-1-en-1-yl)pyrrolidine (2.0 equiv, 60.0 mmol), allyl bromide (1.0 equiv, 30.0 mmol, 2.6 mL), DIEA (2.0 equiv, 60.0 mmol, 10.4 mL) and tert-butyl 2-bromoacetate (2.0 equiv, 60.0 mmol, 8.8 mL). Purification of the crude product by flash column chromatography (5% ethyl acetate in hexane) yielded pure tert-butyl 2-(3-allyl-2-oxocyclopentyl)acetate (3.2 g, 45% yield, pale yellow oil).

$^1$H NMR (300 MHz, $CDCl_3$): δ 5.83-5.62 (m, 1H), 5.13-4.93 (m, 2H), 2.70-1.90 (m, 9H), 1.42 (s, 9H). $^{13}$C NMR (75 MHz, $CDCl_3$): δ 219.6, 171.2, 135.7, 116.5, 80.7, 48.4, 46.1, 35.4, 34.2, 28.1, 27.2, 27.1. IR (neat): 2976, 1725, 1640, 1455, 1415, 1393, 1366, 1255, 1147, 915, 849 cm$^{-1}$. HRMS (m/z) calcd for $C_{14}H_{22}O_3Na$ ([M+Na]$^+$): 261.1461; found: 261.1467.

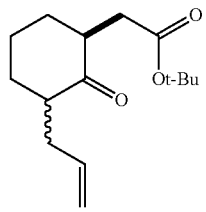 [SMILES: C=CCC1CCC[C@@H](CC(=O)OC(C)(C)C)C1=O]

tert-butyl 2-(3-allyl-2-oxocyclohexyl)acetate

General procedure A was applied using 1-(1-cyclohexen-1-yl)pyrrolidine (1.0 equiv, 22.0 mmol, 3.5 mL), allyl bromide (1.0 equiv, 22.0 mmol, 1.9 mL), DIEA (1.0 equiv, 22.0 mmol, 4.0 mL) and tert-butyl 2-bromoacetate (0.85 equiv, 18.7 mmol, 2.8 mL). Purification of the crude product by flash column chromatography (5% ethyl acetate in hexane) yielded pure tert-butyl 2-(3-allyl-2-oxocyclopentyl)acetate (2.7 g, 55% yield, colorless oil).

$^1$H NMR (300 MHz, $CDCl_3$): δ 5.85-5.63 (m, 1H), 5.10-4.90 (m, 2H), 2.95-2.75 (m, 1H), 2.68 (dd, J=16.3, 7.4 Hz, 1H), 2.6-2.46 (m, 1H), 2.46-2.32 (m, 1H), 2.23-1.67 (m, 6H), 1.43 (s, 9H), 1.42-1.17 (m, 2H). $^{13}$C NMR (75 MHz, $CDCl_3$): δ 211.4, 171.9, 136.5, 116.2, 80.3, 50.2, 47.4, 35.6, 35.1, 34.4, 33.5, 28.0, 25.2. IR (neat): 2977, 2931, 2859, 1709, 1640, 1447, 1416, 1392, 1366, 1276, 1152, 910, 647 cm$^{-1}$. HRMS (m/z) calcd for $C_{15}H_{24}O_3Na$ ([M+Na]$^+$): 275.1618; found: 275.1624.

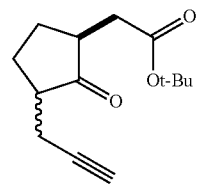 [SMILES: C#CCC1CC[C@@H](CC(=O)OC(C)(C)C)C1=O]

tert-butyl 2-(2-oxo-3-(prop-2-yn-1-yl)cyclopentyl)acetate

General procedure A was applied using freshly prepared 1-(cyclopent-1-en-1-yl)pyrrolidine (2.0 equiv, 60.0 mmol), propargyl bromide (1.0 equiv, 30.0 mmol, 3.2 mL, 80% solution in toluene), DIEA (2.0 equiv, 60.0 mmol, 10.4 mL) and tert-butyl 2-bromoacetate (2.0 equiv, 60.0 mmol, 8.8 mL). Purification of the crude product by flash column chromatography (5% ethyl acetate in hexane) yielded pure tert-butyl 2-(2-oxo-3-(prop-2-yn-1-yl)cyclopentyl)acetate (3.0 g, 42% yield, yellow oil).

$^1$H NMR (300 MHz, $CDCl_3$): δ 2.70-2.10 (m, 8H), 1.95-1.90 (m, 1H), 1.83-1.53 (m, 2H), 1.42 (s, 9H). $^{13}$C NMR (75 MHz, $CDCl_3$): major diastereoisomer: δ 218.0, 171.0, 81.5, 80.8, 69.6, 47.2, 46.0, 35.3, 28.0, 26.8, 26.5, 18.7; minor diastereoisomer, characteristic signals: δ 69.3, 44.7, 35.4, 25.6, 19.2. IR (neat): 3285, 2976, 2876, 1723, 1454, 1425, 1393, 1366, 1255, 1150, 897, 848 cm$^{-1}$. HRMS (m/z) calcd for $C_{14}H_{20}O_3Na$ ([M+Na]$^+$): 259.1305; found: 259.1310.

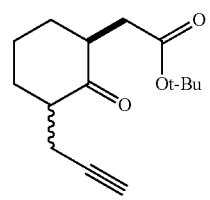 [SMILES: C#CCC1CCC[C@@H](CC(=O)OC(C)(C)C)C1=O]

tert-butyl 2-(2-oxo-3-(prop-2-yn-1-yl)cyclohexyl)acetate

General procedure A was adapted: tert-butyl 2-bromoacetate (0.8 equiv, 14.9 mmol, 2.21 mL) was added to a 1 M solution of 1-(1-cyclohexen-1-yl)pyrrolidine (1.0 equiv, 18.6 mmol, 3 mL) in MeCN at 40° C. After 2.5 h, DIEA (1.0 equiv, 18.6 mmol, 3.24 mL) was added as one portion, followed by slow addition of propargyl bromide (1.0 equiv, 18.6 mmol, 1.96 mL). The mixture was stirred for 12 h at 40° C., then quenched with water and refluxed for 1 h. Purification of the crude product by flash column chromatography (5% ethyl acetate in hexane) yielded pure tert-butyl 2-(2-oxo-3-(prop-2-yn-1-yl)cyclohexyl)acetate (1.4 g, 30%, light yellow wax).

¹H NMR (300 MHz, CDCl₃): δ 2.92-2.76 (m, 1H), 2.70 (dd, J=16.5, 7.4 Hz, 1H), 2.64-2.51 (m, 2H), 2.50-2.38 (m, 1H), 2.27-2.12 (m, 2H), 2.07 (dd, J=16.4, 5.9 Hz, 1H), 1.99-1.70 (m, 3H), 1.46-1.35 (m, 11H). ¹³C NMR (75 MHz, CDCl₃): δ 210.0, 171.8, 82.5, 80.4, 69.4, 49.3, 47.2, 35.4, 34.5, 34.0, 28.0, 25.0, 19.0. IR (neat): 3320, 2979, 2926, 2359, 1722, 1704, 1365, 1277, 1231, 1151, 1109, 1068, 844, 661 cm⁻¹. HRMS (m/z) calcd for $C_{15}H_{22}O_3$ ([M+Na]⁺): 273.1461; found: 273.1468.

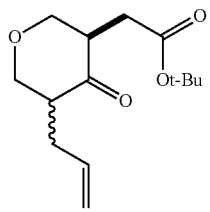

tert-butyl 2-(5-allyl-4-oxotetrahydro-2H-pyran-3-yl)acetate

General procedure A was applied using freshly prepared 1-(3,6-dihydro-2H-pyran-4-yl)pyrrolidine (1.0 equiv, 20.0 mmol), allyl bromide (1.0 equiv, 20.0 mmol, 1.8 ml), DIEA (1.0 equiv, 20.0 mmol, 3.5 ml) and tert-butyl 2-bromoacetate (1.0 equiv, 20.0 mmol, 2.4 ml). Purification of the crude product by flash column chromatography (15% ethyl acetate in hexane) yielded pure tert-butyl 2-(5-allyl-4-oxotetrahydro-2H-pyran-3-yl)acetate (1.96 g, 39% yield, light yellow oil).

¹H NMR (300 MHz, CDCl₃): δ 5.84-5.62 (m, 1H), 5.07-4.97 (m, 2H), 4.31-4.22 (m, 2H), 3.40-3.21 (m, 2H), 3.18-3.01 (m, 1H) 2.79-2.50 (m, 3H), 2.06-1.83 (m, 2H), 1.44 (s, 1H). ¹³C NMR (75 MHz, CDCl₃): δ 207.1, 170.9, 135.1, 116.8, 80.8, 73.3, 73.0, 50.0, 47.6, 30.9, 29.0, 28.0

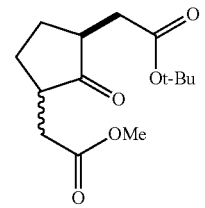 [SMILES: COC(=O)CC1CC[C@@H](CC(=O)OC(C)(C)C)C1=O]

tert-butyl 2-(3-(2-methoxy-2-oxoethyl)-2-oxocyclopentyl)acetate

General procedure A was applied using freshly prepared 1-(cyclopent-1-en-1-yl)pyrrolidine (2.0 equiv, 85.0 mmol), methyl bromoacetate (1.0 equiv, 42.5 mmol), DIEA (2.0 equiv, 85.0 mmol) and t-butyl bromoacetate (2.0 equiv, 85.0 mmol). Purification of the crude product by flash column chromatography (20% diethylether in hexane) yielded pure tert-butyl 2-(3-(2-methoxy-2-oxoethyl)-2-oxocyclopentyl)acetate as a mixture of diastereoisomers (6.9 g, 60% yield, colorless oil).

¹H NMR (300 MHz, CDCl₃): δ 5.84-5.62 (m, 1H), 5.07-4.97 (m, 2H), 4.31-4.22 (m, 2H), 3.40-3.21 (m, 2H), 3.18-3.01 (m, 1H) 2.79-2.50 (m, 3H), 2.06-1.83 (m, 2H), 1.44 (s, 1H). ¹³C NMR (75 MHz, CDCl₃): δ 207.1, 170.9, 135.1, 116.8, 80.8, 73.3, 73.0, 50.0, 47.6, 30.9, 29.0, 28.0 FTIR (thin film): cm⁻¹. HRMS (m/z) calcd for $C_{14}H_{22}O_4Na$ ([M+Na]⁺); found.

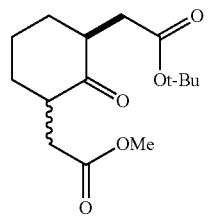 [SMILES: COC(=O)CC1CCC[C@@H](CC(=O)OC(C)(C)C)C1=O]

tert-butyl 2-(3-(2-methoxy-2-oxoethyl)-2-oxocyclohexyl)acetate

General procedure A was applied using 1-(cyclohex-1-en-1-yl)pyrrolidine (1.0 equiv, 31.0 mmol), methyl-2-bromoacetate (1.0 equiv, 2.9 mL), DIEA (1.0 equiv, 5.4 mL) and tert-butyl 2-bromoacetate (1.0 equiv, 4.6 mL). Purification of the crude product by flash column chromatography (20% diethylether in hexane) yielded pure tert-butyl 2-(3-(2-methoxy-2-oxoethyl)-2-oxocyclohexyl)acetate as a mixture of diastereoisomers (4.5 g, 51% yield, colorless oil).

¹H NMR (300 MHz, CDCl₃): δ 3.59 (s, 3H), 2.87-2.57 (m, 4H), 2.13-1.97 (m, 4H), 1.83-1.77 (m, 2H), 1.40-1.29 (m, 11H). ¹³C NMR (75 MHz, CDCl₃): major diastereoisomer: δ 210.1, 172.7, 171.5, 80.2, 51.4, 47.0, 46.8, 35.4, 34.3₄, 34.3, 34.0, 27.8, 24.9; minor diastereoisomer, characteristic signals: 172.8, 46.9, 41.6, 36.1, 34.0, 33.7, 25.0.

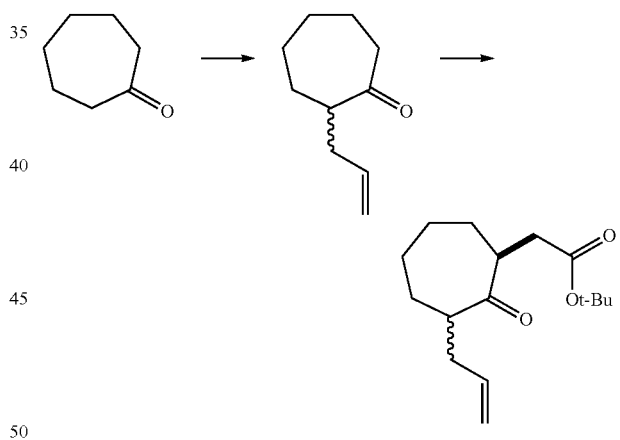

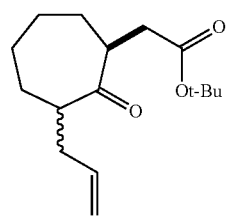 [SMILES: C=CCC1CCCC[C@@H](CC(=O)OC(C)(C)C)C1=O]

tert-butyl 2-(3-allyl-2-oxocycloheptyl)acetate

To a 1 M solution of freshly prepared 1-(cyclohept-1-en-1-yl)pyrrolidine (1.0 equiv, 42.4 mmol) in MeCN, allyl bromide (1.0 equiv, 42.4 mmol, 3.66 mL) was added dropwise. The solution was stirred for 12 h at room temperature, quenched with H₂O and refluxed for 2 h. After cooling to room temperature, the aqueous layer was extracted with diethyl ether. The combined organic layers were dried (Na₂SO₄), filtered and concentrated in vacuo. Purification of the crude product by flash column chromatography (10% diethyl ether in hexane) afforded pure 2-allylcycloheptanone (3.67 g, 57% yield, colorless oil).

2-allylcycloheptanone (1.0 equiv, 14.0 mmol, 2.3 g) was added to in situ prepared LDA (1.1 equiv) at −78° C. and the mixture was stirred for 90 min at −78° C. Tert-butyl 2-bromoacetate (2.0 equiv, 28.0 mmol, 4.16 mL) was added slowly. The reaction mixture was allowed to reach room temperature over 12 h, and was then quenched with water. The aqueous layer was extracted with diethyl ether; the combined organic layers were dried (Na₂SO₄), filtered and concentrated in vacuo. Purification of the crude compound by flash column chromatography (15% diethyl ether in hexane) yielded tert-butyl 2-(3-allyl-2-oxocycloheptyl)acetate (1.79 g, 49% yield, colorless oil).

IR (neat): 2977, 2926, 2855, 1725, 1701, 1639, 1454, 1365, 1284, 1152, 993, 941, 912, 857, 758. HRMS (m/z) calcd for $C_{16}H_{26}O_2Na$ ([M+Na]⁺): 289.1774; found: 289.1779.

General Procedure B: Olefination of α,α'-Dialkylated Cyclic Ketones (Wittig Reaction)

Methyltriphenylphosphonium bromide (2.0 equiv) and potassium tert-butoxide (2.0 equiv) were stirred at 50° C. in dry THF (0.4 M) for 2 h. A 3 M solution of α,α'-dialkylated cyclic ketone (1.0 equiv) in dry THF was added dropwise at 0° C. and the mixture stirred for 2 h at room temperature. Water was added, and the aqueous layer was extracted twice with diethyl ether. The combined organic layers were dried (Na₂SO₄), filtered, and the solvent was removed under reduced pressure. The residue was purified by column chromatography (silica gel, hexane/ethyl acetate) to yield the dialkylated cycloalkyl methylene.

General Procedure C: Oxymercuration

A 0.1 M solution of the dialkylated cycloalkyl methylene (1.0 equiv) in methanol was added to a suspension of HgO (0.2 equiv) in 4% H₂SO₄, and the reaction mixture was stirred at room temperature for 1 h. The reaction mixture was then poured into water and extracted twice with ethyl acetate. The combined organic layers were washed with brine, dried (Na₂SO₄) and filtered. The solvent was removed under reduced pressure, and the residue was purified by column chromatography (silica gel, hexane/ethyl acetate).

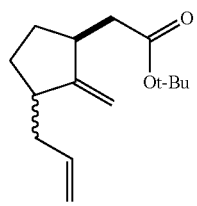 [SMILES: C=CCC1CC[C@@H](CC(=O)OC(C)(C)C)C1=C]

tert-butyl 2-(3-allyl-2-methylenecyclopentyl)acetate

General procedure B was applied using tert-butyl 2-(3-allyl-2-oxocyclopentyl)acetate (4.5 mmol, 1.1 g), methyltriphenylphosphonium bromide (9.0 mmol, 3.2 g) and potassium tert-butoxide (9.0 mmol, 1.0 g). Purification of the residue by flash column chromatography (5% ethyl acetate in hexane) yielded pure tert-butyl 2-(3-allyl-2-methylenecyclopentyl)acetate as an unseparable mixture of diastereoisomers (640 mg, 60% yield, colorless oil).

¹H NMR (300 MHz, CDCl₃): δ 5.90-5.70 (m, 1H), 5.09-4.93 (m, 2H), 4.90-4.80 (m, 2H), 2.90-2.69 (m, 1H), 2.57-2.24 (m, 3H), 2.21-1.70 (m, 4H), 1.47-1.36 (m, 10H), 1.29-1.18 (m, 1H). ¹³C NMR (75 MHz, CDCl₃): major diastereoisomer: δ 172.4, 158.4, 137.4, 115.6, 105.0, 80.1, 43.2, 40.9, 40.9, 39.2, 30.1, 29.2, 28.1; minor diastereoisomer, characteristic signals: δ 158.2, 104.6, 43.5, 41.0, 40.7, 39.1, 31.3, 30.5. IR (neat): 2977, 1728, 1640, 1455, 1392, 1367, 1321, 1255, 1144, 993, 947, 911, 883, 845 cm⁻¹. HRMS (m/z) calcd for $C_{15}H_{24}O_2Na$ ([M+Na]⁺): 259.1668; found: 259.1671.

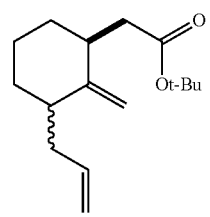 [SMILES: C=CCC1CCC[C@@H](CC(=O)OC(C)(C)C)C1=C]

tert-butyl 2-(3-allyl-2-methylenecyclohexyl)acetate

General procedure B was applied using tert-butyl 2-((1S)-3-allyl-2-oxocyclohexyl)acetate (10.8 mmol, 2.7 g), methyltriphenylphosphonium bromide (21.6 mmol, 7.7 g) and potassium tert-butoxide (21.6 mmol, 2.6 g). Purification of the residue by flash column chromatography (20% diethyl ether in hexane) yielded pure tert-butyl 2-(3-allyl-2-methylenecyclohexyl)acetate as an unseparable mixture of diastereoisomers (2.0 g, 75%, colorless oil)

¹³C NMR (75 MHz, CDCl₃): δ 172.5, 137.7, 115.7, 101.8, 80.1, 43.6, 40.9, 39.2, 37.1, 35.2, 34.8, 28.1, 25.9. IR (neat): 2976, 2924, 2853, 1730, 1640, 1445, 1367, 1340, 1293, 1256, 1140, 993, 949, 909, 886, 850, 760 cm⁻¹. HRMS (m/z) calcd for $C_{16}H_{26}O_2Na$ ([M+Na]⁺): 273.1852; found 273.1829.

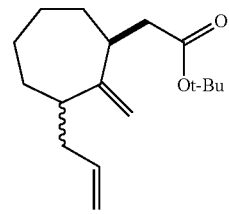 [SMILES: C=CCC1CCCC[C@@H](CC(=O)OC(C)(C)C)C1=C]

tert-butyl 2-(3-allyl-2-methylenecycloheptyl)acetate

General procedure B was applied using tert-butyl 2-(3-allyl-2-oxocycloheptyl)acetate (6.5 mmol, 1.74 g), methyltriphenylphosphonium bromide (17.2 mmol, 6.14 g), potassium tert-butoxide (17.2 mmol, 2.08 g). The reaction required 18 h to go to completion. Purification of the residue by flash column chromatography (5% diethyl ether in hexane) yielded pure tert-butyl 2-(3-allyl-2-methylenecycloheptyl)acetate as an unseparable mixture of diastereoisomers (0.69 g, 40% yield, colorless oil).

$^1$H NMR (300 MHz, CDCl$_3$): δ 5.86-5.64 (m, 1H), 5.05-4.88 (m, 2H), 4.88-4.70 (m, 2H), 2.69-2.03 (m, 6H), 1.97-1.44 (m, 5H), 1.42 (s, 9H), 1.31-1.03 (3H). $^{13}$C NMR (75 MHz, CDCl$_3$): major diastereoisomer: δ 172.2, 155.2, 138.0, 115.2, 106.5, 79.9, 45.7, 42.4, 41.2, 39.2, 35.2, 35.1, 28.1, 28.0, 25.7; minor diastereoisomer, characteristic signals: δ 156.2, 110.4, 44.2, 41.9, 40.5, 39.9, 35.8. IR (neat): 3075, 2977, 2852, 1728, 1639, 1452, 1392, 1366, 1288, 1255, 1130, 993, 949, 908, 888, 847, 760, 670 cm$^{-1}$. HRMS (m/z) calcd for C$_{17}$H$_{28}$O$_2$Na ([M+Na]$^+$): 287.1981; found 287.1989.

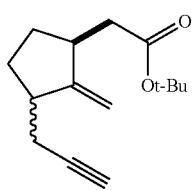 [SMILES: C#CCC1CC[C@@H](CC(=O)OC(C)(C)C)C1=C]

tert-butyl 2-(2-methylene-3-(prop-2-yn-1-yl)cyclopentyl)acetate

General procedure B was applied using tert-butyl 2-(2-oxo-3-(prop-2-yn-1-yl)cyclopentyl)acetate (11.8 mmol, 2.8 g), methyltriphenylphosphonium bromide (25.4 mmol, 9.1 g) and potassium tert-butoxide (25.4 mmol, 2.8 g). Purification of the residue by flash column chromatography (5% ethyl acetate in hexane) yielded pure tert-butyl 2-(2-methylene-3-(prop-2-yn-1-yl)cyclopentyl)acetate as an unseparable mixture of diastereoisomers (2.0 g, 72% yield, yellow oil).

$^1$H NMR (300 MHz, CDCl$_3$): δ 4.97-4.86 (m, 2H), 2.91-2.73 (m, 1H), 2.71-2.56 (m, 1H), 2.51-2.32 (m, 2H), 2.30-2.10 (m, 2H), 2.07-1.80 (m, 3H), 1.70-1.55 (m, 1H), 1.50-1.40 (m, 10H). $^{13}$C NMR (75 MHz, CDCl$_3$): major diastereoisomer: δ 172.2, 157.1, 105.8, 83.4, 80.2, 68.6, 42.7, 40.8, 40.7, 30.0, 29.5, 28.1, 23.8; minor diastereoisomer, characteristic signals: δ 156.9, 105.5, 68.8, 42.7, 41.0, 40.6, 31.1, 30.6, 23.6. IR (neat): 3292, 2976, 1724, 1456, 1393, 1367, 1255, 1150, 948, 890, 843 cm$^{-1}$. HRMS (m/z) calcd for C$_{15}$H$_{22}$O$_2$Na ([M+Na]$^+$): 257.1512; found: 257.1515.

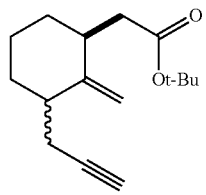 [SMILES: C#CCC1CCC[C@@H](CC(=O)OC(C)(C)C)C1=C]

tert-butyl 2-(2-methylene-3-(prop-2-yn-1-yl)cyclohexyl)acetate

General procedure B was applied using tert-butyl 2-(2-oxo-3-(prop-2-yn-1-methyltriphenylphosphonium bromide (10.0 mmol, 3.9 g), potassium tert-butoxide (10.0 mmol, 1.3 g). Purification of the residue by flash column chromatography (5% ethyl acetate in hexane) yielded pure tert-butyl 2-(2-methylene-3-(prop-2-yn-1-yl)cyclohexyl)acetate as an unseparable mixture of diastereoisomers (1.1 g, 78% yield, yellow oil).

$^1$H NMR (300 MHz, CDCl$_3$): δ 4.68-4.64 (s, 1H), 4.64-4.59 (s, 1H) 2.56-2.34 (m, 3H), 2.29-2.08 (m, 4H), 2.01-1.94 (m, 2H), 1.65-1.40 (m, 2H), 1.43 (s, 9H) 1.15-0.96 (m, 2H). $^{13}$C NMR (75 MHz, CDCl$_3$): δ 172.3, 153.5, 102.2, 83.4, 80.2, 69.3, 42.9, 40.9, 39.3, 34.9, 34.5, 28.0, 25.9, 22.3. IR (neat): 3308, 2976, 2926, 2855, 2118, 1727, 1643, 1447, 1351, 1341, 1293, 1250, 1135, 1125, 1088, 951, 887, 850, 760 cm$^{-1}$. HRMS (m/z) calcd for C$_{16}$H$_{24}$O$_2$Na ([M+Na]$^+$): 271.1668; found 271.1677.

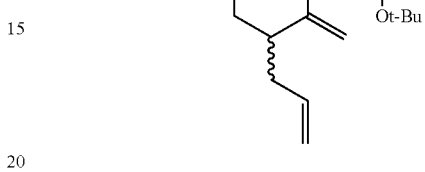

tert-butyl 2-(5-allyl-4-methylenetetrahydro-2H-pyran-3-yl)acetate

General procedure B was applied using tert-butyl 2-(5-allyl-4-oxotetrahydro-2H-pyran-3-yl)acetate (7.7 mmol, 1.96 gr), methyltriphenylphosphonium bromide (15.4 mmol, 5.5 g), and potassium tert-butoxide (15.4 mmol, 1.73 g). Purification of the residue by flash column chromatography (10% ethyl acetate in hexane) yielded tert-butyl 2-(5-allyl-4-methylenetetrahydro-2H-pyran-3-yl)acetate (1.0 g, 51% yield, pale yellow oil).

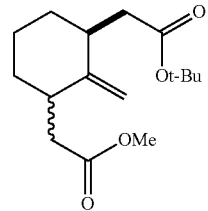 [SMILES: C=C1C(CC(=O)OC)CCC[C@H]1CC(=O)OC(C)(C)C]

tert-butyl 2-(3-(2-methoxy-2-oxoethyl)-2-methylenecyclohexyl)acetate

General procedure B was applied using tert-butyl 2-(3-(2-methoxy-2-oxoethyl)-2-oxocyclohexyl)acetate (15.8 mmol, 4.5 g), methyltriphenylphosphonium bromide (31.7 mmol, 11.3 g) and potassium tert-butoxide (31.7 mmol, 3.6 g). Purification of the residue by flash column chromatography (10% diethylether in hexane) yielded pure tert-butyl-2-(3-(2-methoxy-2-oxoethyl)-2-methylenecyclohexyl)acetate as a mixture of diastereoisomers (2.5 g, 63% yield, colorless oil).

$^1$H NMR (300 MHz, CDCl$_3$): δ 4.41 and 4.40 (2s, 2H), 3.49 (s, 3H), 2.48-2.25 (m, 4H), 2.16-1.99 (m, 2H), 1.76-1.40 (m, 4H), 1.27 (s, 9H), 0.94-0.80 (m, 2H). $^{13}$C NMR (75 MHz, CDCl$_3$): major diastereoisomer: δ 172.8, 171.6, 153.5, 101.4, 79.6, 51.0, 40.6, 40.4, 38.9, 37.5, 34.7, 34.6, 27.7, 25.5; minor diastereoisomer, characteristic signals: 172.6, 171.4, 151.9, 79.5$_9$, 38.6, 38.1, 37.9, 37.3, 32.8$_2$, 32.8$_0$. IR (neat): 3292, 2976, 1724, 1456, 1393, 1367, 1255, 1150, 948, 890, 843 cm$^{-1}$. HRMS (m/z) calcd for C$_{15}$H$_{22}$O$_2$Na ([M+Na]$^+$): 257.15120; found: 257.15152.

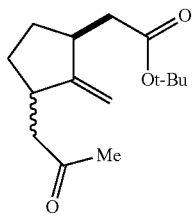 [SMILES: C=C1C(CC(C)=O)CC[C@H]1CC(=O)OC(C)(C)C]

tert-butyl 2-(2-methylene-3-(2-oxopropyl)cyclopentyl)acetate

General procedure C was applied using tert-butyl 2-(2-methylene-3-(prop-2-yn-1-yl)cyclopentyl)acetate (1.7 mmol, 0.4 g) and HgO (0.3 mmol, 0.07 g) in 4% $H_2SO_4$ (7 mL). Purification of the crude product by flash column chromatography (5% ethyl acetate in hexane) yielded pure tert-butyl 2-(2-methylene-3-(2-oxopropyl)cyclopentyl)acetate as an unseparable mixture of diastereoisomers (267 mg, 62% yield, pale yellow oil).

$^1$H NMR (300 MHz, $CDCl_3$): δ 4.89-4.74 (m, 2H), 2.98-2.78 (m, 1H), 2.69 (td, J=17.9, 4.9 Hz, 1H), 2.55-2.33 (m, 2H), 2.25-1.93 (m, 5H), 1.48-1.16 (m, 13H). $^{13}$C NMR (75 MHz, $CDCl_3$): major diastereoisomer: δ 208.2, 172.1, 158.0, 104.9, 80.3, 49.1, 40.9, 40.4, 39.2, 30.3, 30.2, 30.0, 28.1; minor diastereoisomer, characteristic signals: δ 104.8, 49.1, 40.8, 40.6, 39.5, 31.5, 31.3. IR (neat): 2976, 1718, 1650, 1392, 1324, 1255, 1149, 1078, 950, 885, 845 cm$^{-1}$. HRMS (m/z) calcd for $C_{15}H_{24}O_3Na$ ([M+Na]$^+$): 275.1618; found: 275.1620.

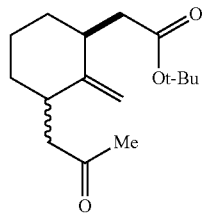 [SMILES: C=C1C(CC(C)=O)CCC[C@H]1CC(=O)OC(C)(C)C]

tert-butyl 2-(2-methylene-3-(2-oxopropyl)cyclohexyl)acetate

General procedure C was applied using tert-butyl 2-(2-methylene-3-(prop-2-yn-1-yl)cyclohexyl)acetate (2.8 mmol, 0.7 g) and HgO (0.6 mmol, 0.1 g) in 4% $H_2SO_4$ (11 ml). The reaction requires 3.5 h to go to completion. Purification of the crude product by flash column chromatography (30% diethyl ether in hexane) yielded tert-butyl 2-(2-methylene-3-(2-oxopropyl)cyclohexyl)acetate as an unseparable mixture of diastereoisomers (0.47 g, 55% yield, colorless oil).
1H NMR (300 MHz, $CDCl_3$): δ 4.56 (s, 1H), 4.49 (s, 1H), 2.69 (dd, J=54.7, 8.3 Hz, 1H), 2.59-2.32 (m, 4H), 2.24-2.16 (m, 1H), 2.15 (s, 3H), 1.92-1.72 (m, 3H), 1.64-1.54 (m, 1H), 1.42 (s, 9H), 1.10-0.90 (m, 2H). $^{13}$C NMR (75 MHz, $CDCl_3$): δ 208.3, 172.3, 154.1, 101.8, 80.2, 47.2, 40.9, 39.8, 39.4, 35.2, 35.0, 30.2, 28.0, 25.9. IR (neat): 2976, 2925, 1720, 1641, 1391, 1366, 1292, 1255, 1150, 1122, 1025, 946, 887, 846, 760. HRMS (m/z) calcd for $C_{16}H_{26}O_3H$ ([M+H]$^+$): 267.19547; found 267.19550.

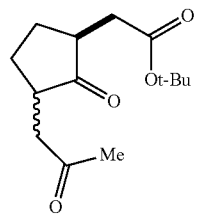 [SMILES: CC(=O)CC1CC[C@@H](CC(=O)OC(C)(C)C)C1=O]

tert-butyl 2-(2-oxo-3-(2-oxopropyl)cyclopentyl)acetate

General procedure C was applied using tert-butyl 2-(2-oxo-3-(prop-2-yn-1-yl)cyclopentyl)acetate (8.9 mmol, 2.1 g) and HgO (1.8 mmol, 0.39 g) in 4% $H_2SO_4$ (36 mL). Purification of the crude product by flash column chromatography (20% ethyl acetate in hexane) yielded pure tert-butyl 2-(2-oxo-3-(2-oxopropyl)cyclopentyl)acetate (1.6 g, 70% yield, colorless oil).

$^1$H NMR (300 MHz, $CDCl_3$): δ 2.89 (td, J=18.1, 3.2 Hz, 1H), 2.70-2.32 (m, 5H), 2.30-2.16 (m, 2H), 2.14 (s, 3H), 1.78-1.47 (m, 2H), 1.42 (s, 9H). $^{13}$C NMR (75 MHz, $CDCl_3$): major diastereoisomer: δ 219.6, 206.4, 171.1, 80.8, 45.3, 44.6, 43.5, 35.5, 30.0, 28.1, 27.5, 27.4; minor diastereoisomer, characteristic signals: δ 206.5, 171.4, 44.1, 44.0, 43.0, 36.1, 26.5, 26.3. IR (neat): 2975, 1716, 1454, 1393, 1366, 1326, 1254, 1151, 848 cm$^{-1}$. HRMS (m/z) calcd for $C_{14}H_{23}O_4Na$ ([M+H]$^+$): 255.1591; found: 255.1594.

tert-butyl 2-(3-(2-methylallyl)-2-methylenecyclopentyl)acetate

General procedure B was adapted using tert-butyl 2-(2-oxo-3-(2-oxopropyl)cyclopentyl)acetate (5.1 mmol, 1.3 g), and a larger amount of methyltriphenylphosphonium bromide (4.0 equiv, 20.4 mmol, 7.3 g) and potassium tert-butoxide (20.4 mmol, 2.3 g). Purification of the residue by flash column chromatography (hexane) yielded pure tert-butyl 2-(3-(2-methylallyl)-2-methylenecyclopentyl)acetate as an unseparable mixture of diastereoisomers (785 mg, 61% yield, yellow oil).

$^1$H NMR (300 MHz, $CDCl_3$): δ 4.89-4.79 (m, 2H), 4.75-4.65 (m, 2H), 2.91-2.71 (m, 1H), 2.69-2.56 (m, 1H), 2.48 (ddd, J=15.1, 14.0, 5.4 Hz, 1H), 2.38-2.08 (m, 2H), 2.01-1.79 (m, 2H), 1.73 (s, 3H), 1.48-1.35 (m, 11H), 1.29-1.18 (m, 1H). $^{13}$C NMR (75 MHz, $CDCl_3$): major diastereoisomer: δ 172.4, 159.1, 144.6, 111.3, 104.7, 80.2, 43.7, 41.4, 41.0, 41.0, 30.0, 29.3, 28.1, 22.2; minor diastereoisomer, characteristic signals: δ 111.2, 104.5, 43.8, 41.8, 40.9, 40.8, 31.2, 30.8. IR (neat): 2977, 2932, 1728, 1649, 1454, 1392, 1367, 1256, 1149, 951, 884, 846 cm$^{-1}$. HRMS (m/z) calcd for $C_{15}H_{26}O_2Na$ ([M+Na]$^+$): 273.1825; found: 273.1826.

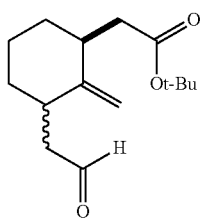 [SMILES: C=C1C(CC=O)CCC[C@H]1CC(=O)OC(C)(C)C]

tert-butyl
2-(2-methylene-3-(2-oxoethyl)cyclohexyl)acetate

To the 0.1 M solution of tert-butyl 2-(3-(2-methoxy-2-oxoethyl)-2-methylenecyclohexyl)acetate (1.0 equiv, 4.6 mmol) in dry diethyl ether was added 1 M solution of diisobutylaluminium hydride (1.4 equiv, 6.4 mmol) dropwise at −78° C. After the addition, the stirring was continued for 1 h at the same temperature. The reaction was quenched by the slow addition of water (7.0 equiv, 32.2 mmol). The reaction mixture was dried over $Na_2SO_4$ and filtered through celite. Purification of the residue by flash column chromatography (5% diethylether in hexane) yielded pure tert-butyl 2-(2-methylene-3-(2-oxoethyl)cyclohexyl)acetate as a mixture of diastereoisomers (0.58 g, 58% yield, colorless oil).

$^1$H NMR (300 MHz, $CDCl_3$): δ 9.73 (t, 1H), 4.61 and 4.52 (2s, 2H), 2.72-2.18 (m, 6H), 1.9-1.57 (m, 4H), 1.42 (s, 9H), 1.24-1.01 (m, 2H). $^{13}$C NMR (75 MHz, $CDCl_3$): major diastereoisomer: δ 202.4, 172.1, 153.4, 102.7, 80.3, 46.9, 40.9, 39.3, 38.7, 35.3, 34.8, 28.0, 25.9; minor diastereoisomer, characteristic signals: 107.1, 46.4, 39.0, 36.1, 33.4, 33.07.

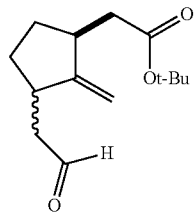 [SMILES: C=C1C(CC=O)CC[C@H]1CC(=O)OC(C)(C)C]

tert-butyl
2-(2-methylene-3-(2-oxoethyl)cyclopentyl)acetate

To the 0.1 M solution of tert-butyl 2-(3-(2-methoxy-2-oxoethyl)-2-methylenecyclopentyl)acetate (1.0 equiv, 7.0 mmol, 1.9 g) in dry diethyl ether was added 1 M solution of diisobutylaluminium hydride (1.4 equiv, 9.8 mmol) dropwise at −78° C. After the addition, the stirring was continued for 1 h at the same temperature. The reaction was quenched by the slow addition of water (7.0 equiv, 49.0 mmol). The reaction mixture was dried over $Na_2SO_4$ and filtered through celite. Purification of the residue by flash column chromatography (5% diethylether in hexane) yielded pure tert-butyl 2-(2-methylene-3-(2-oxoethyl)cyclopentyl)acetate as a mixture of diastereoisomers (0.80 g, 48% yield, colorless oil).

2. Cyclization Procedures

General Procedure D: Iodolactonization

To a 0.1 M solution of key precursor (1.0 equiv) in MeCN, $I_2$ (1.0-1.1 equiv) was added. After stirring for 1-2 h at room temperature, the reaction mixture was quenched with aqueous saturated sodium thiosulfate. The aqueous layer was extracted with dichloromethane (3×). The combined organic layers were dried ($Na_2SO_4$), filtered, and the solvent was removed under reduced pressure. Purification of the residue by column chromatography (silica gel, hexane/diethyl ether or ethyl acetate) allows isolation of the two pure diastereoisomers of iodolactone.

The reaction was monitored by GCMS. Decomposition of the desired iodolactones is observed when the reaction is not quenched immediately upon completion.

General Procedure E: Pd-Catalyzed Cyclization

Iodolactone (1.0 equiv, 0.5 mmol), $Pd_2(MeO-dba)_3$ (0.075 equiv, 0.04 mmol, 41 mg), SIMes-$HBF_4$ (0.25 equiv, 0.12 mmol, 49 mg) and $Cs_2CO_3$ (1.1 equiv, 0.55 mmol, 179 mg) were weighed into an oven-dried sealed flask. The flask was then evacuated and back-filled with nitrogen. After addition of dry MeCN (0.1 M, 5 mL), the reaction mixture was stirred at room temperature for 5 minutes, and then placed in a preheated oil bath at 100° C. and stirred for 16 h. At the end of this time, the flask was allowed to cool to room temperature, the contents diluted with EtOAc and the mixture filtered through a plug of silica. The solution was then concentrated under reduced pressure and the residue purified by column chromatography (silica gel, hexane/diethyl ether) to afford the desired tricyclic product.

General Procedure F: $SmI_2$ Mediated Cyclization with Carbonyl

To a premixed solution of $SmI_2$ in THF (0.1 M, 5.0 equiv, 2.5 mmol, 25.5 ml) and HMPA (10.0 equiv, 5.0 mmol, 20.9 ml), iodolactone (1.0 equiv, 0.5 mmol) in dry THF (0.1 M, 5.1 ml) was added dropwise at room temperature. The solution was heated to 40° C., stirred for 2 h under inert atmosphere and quenched with aqueous saturated $K_2CO_3$. The mixture was diluted with diethyl ether, the phases separated and the aqueous layer re-extracted with diethyl ether. The combined organic phases were dried ($Na_2SO_4$), filtered, and the solvent was removed under reduced pressure. Purification of the residue by column chromatography (silica gel, hexane/dichloromethane) yields the desired tricyclic product.

General Procedure G: $SmI_2$ Mediated Cyclization with Olefins

To a solution of iodolactone (1.0 equiv, 0.5 mmol) in dry THF (0.04 M, 12 mL), HMPA (19.0 equiv, 9.5 mmol, 1.6 mL) and MeOH (10.0 equiv, 5.0 mmol, 0.2 mL) at room temperature was added dropwise a solution of $SmI_2$ in THF (0.1 M, 4.0 equiv, 2.0 mmol, 20 mL). The reaction mixture was stirred under inert atmosphere for 2 h and quenched with aqueous saturated $NH_4Cl$. The mixture was diluted with diethyl ether, the phases separated and the aqueous layer re-extracted with diethyl ether. The combined organic phases were washed with saturated aqueous solutions of $CuSO_4$, $Na_2S_2O_3$ and brine, dried ($Na_2SO_4$), filtered, and the solvent was removed under reduced pressure. Purification of the residue by column chromatography (silica gel, hexane/dichloromethane) yields the desired tricyclic product.

General Procedure H: $Bu_3SnH$ Mediated Radical Cyclization

To a refluxing solution of iodolactone (1.0 equiv, 0.5 mmol) in toluene (0.01 M, 50 mL) was added dropwise a solution of $Bu_3SnH$ (1.1 equiv, 0.55 mmol, 0.15 mL) and AIBN (0.1 equiv, 0.05 mmol, 8 mg) in toluene (5 mL). The solution was refluxed for 1 h. After cooling to room temperature, the mixture was diluted with diethyl ether, a slight excess of DBU was added, followed by dropwise addition of a 0.1 M ethereal solution of iodine until the iodine color persists. The solution was filtered rapidly through a short plug of silica eluting with diethyl ether. The solution was then concentrated under reduced pressure and the residue purified by column chromatography (silica gel, hexane/diethyl ether or ethyl acetate) to afford the desired tricyclic product.

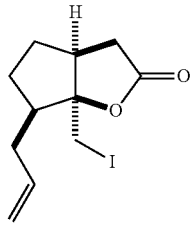

6-allyl-6a-(iodomethyl)hexahydro-2H-cyclopenta[b]furan-2-one

General procedure D was applied using tert-butyl 2-(3-allyl-2-methylenecyclopentyl)acetate (2.1 mmol, 0.50 g) and I2 (2.1 mmol, 0.54 g). Purification of the crude product by flash column chromatography (20% diethyl ether in hexane) yielded the two pure diastereoisomers (83% total yield, dr 67:33).

Major diastereoisomer (yellow oil):

$^1$H NMR (300 MHz, CDCl$_3$): δ 5.78 (ddt, J=17.1, 10.0, 7.0 Hz, 1H), 5.09 (dd, J=17.1, 1.7 Hz, 1H), 5.02 (dd, J=10.0, 1.7 Hz, 1H), 3.67 (d, J=10.8 Hz, 1H), 3.35 (d, J=10.8 Hz, 1H), 3.05 (dd, J=18.7, 10.9 Hz, 1H), 2.89-2.76 (m, 1H), 2.40-2.27 (m, 1H), 2.25-1.95 (m, 4H), 1.93-1.78 (m, 1H), 1.62-1.36 (m, 2H). $^{13}$C NMR (75 MHz, CDCl$_3$): δ 176.5, 136.5, 116.6, 94.5, 48.2, 44.1, 37.7, 33.2, 32.2, 31.2, 12.7. IR (neat): 2953, 1767, 1640, 1451, 1412, 1242, 1201, 1155, 1093, 1035, 995, 957, 912 cm$^{-1}$. HRMS (m/z) calcd for C$_{11}$H$_{16}$IO$_2$ ([M+H]$^+$): 307.0189; found: 307.0187.

Minor diastereoisomer (pale yellow oil):

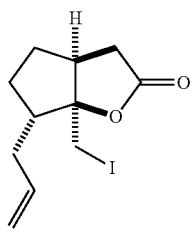

1H NMR (300 MHz, CDCl$_3$): δ 5.83 (m, 1H), 5.14-5.02 (m, 2H), 3.62 (d, J=11.0 Hz, 1H), 3.32 (d, J=11.0 Hz, 1H), 3.05 (dd, J=18.6, 10.5 Hz, 1H), 2.71-2.57 (m, 1H), 2.43-2.11 (m, 4H), 2.06-1.88 (m, 2H), 1.54-1.38 (m, 2H). $^{13}$C NMR (75 MHz, CDCl$_3$): δ 176.4, 135.9, 116.9, 94.9, 49.2, 44.1, 38.1, 33.1, 32.3, 29.7, 12.5. IR (neat): 2927, 1766, 1640, 1452, 1415, 1235, 1199, 1155, 1011, 993, 915 cm$^{-1}$. HRMS (m/z) calcd for C$_{11}$H$_{16}$IO$_2$ ([M+H]$^+$): 307.0189; found: 307.0192.

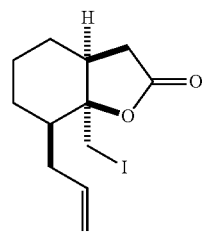

4-allyl-3a-(iodomethyl)hexahydro-1H-inden-2(3H)-one

General procedure D was applied using tert-butyl 2-(3-allyl-2-methylenecyclohexyl)acetate (1 equiv, 1.6 mmol, 0.40 g) and I$_2$ (1 equiv, 1.6 mmol, 0.41 g). Purification of the crude product by flash column chromatography (20% diethyl ether in hexane) yielded the two pure diastereoisomers (0.28 g, 55% total yield, dr 86:14).

Major diastereoisomer (white solid): M.p. 31-33° C.

$^1$H NMR (500 MHz, CDCl$_3$): δ 5.93-5.69 (m, 1H), 5.22-5.01 (m, 2H), 3.60 (d, J=10.8 Hz, 1H), 3.33 (d, J=10.9 Hz, 1H), 2.83 (dd, J=17.7, 7.6 Hz, 1H), 2.80-2.67 (m, 1H), 2.48-2.34 (m, 1H), 2.30-2.14 (m, 2H), 2.12-1.96 (m, 1H), 1.94-1.83 (m, 1H), 1.74-1.60 (m, 1H), 1.38-1.27 (m, 1H), 1.24-1.09 (m, 2H). $^{13}$C NMR (75 MHz, CDCl$_3$): δ 175.9, 136.6, 116.8, 86.9, 38.8, 37.4, 36.7, 34.1, 29.0, 25.5, 21.6, 9.8. IR (neat): 2936, 2857, 1772, 1703, 1639, 1443, 1361, 1215, 1187, 1147, 1089, 999, 949, 917, 884, 762, 694 cm$^{-1}$. HRMS (m/z) calcd for C$_{12}$H$_{17}$IO$_2$ ([M+H]$^+$): 321.0346; found: 321.0350.

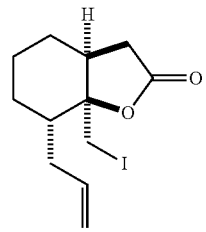

Minor diastereoisomer (white solid):

$^{13}$C NMR (75 MHz, CDCl$_3$): δ 175.0, 136.1, 117.4, 85.5, 42.2, 40.6, 34.1, 32.6, 27.2, 24.0, 20.1, 9.7 HRMS (m/z) calcd for C$_{12}$H$_{17}$IO$_2$ ([M+H]$^+$): 321.0346; found: 321.0350 X-Ray crystal data available (not shown).

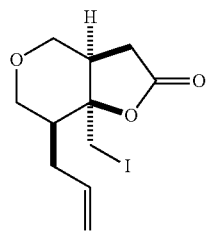

7-allyl-7a-(iodomethyl)hexahydro-2H-furo[3,2-c]pyran-2-one

General procedure D was applied using tert-butyl 2-(5-allyl-4-methylenetetrahydro-2H-pyran-3-yl)acetate (1.0 equiv, 3.8 mmol, 850 mg) and 12 (1.0 equiv, 3.8 mmol, 850 mg). Purification of the crude product by flash column chromatography (30% diethyl ether in hexane) yielded the two pure diastereoisomers Major diastereoisomer (white solid):
$^1$H NMR (500 MHz, CDCl$_3$): δ 5.84-5.64 (m, 1H), 5.15-5.00 (m, 2H), 4.01-3.87 (m, 1H), 3.87-3.75 (m, 1H), 3.62-3.51 (m, 1H), 3.35-3.06 (m, 3H), 2.90-2.70 (m, 2H), 2.61-2.45 (m, 1H), 2.41-2.26 (m, 1H), 2.21-2.05 (m, 1H), 2.03-1.85 (m, 1H). $^{13}$C NMR (75 MHz, CDCl$_3$): δ 174.8, 135.1, 117.5, 84.4, 67.7, 66.9, 37.2, 36.6, 32.6, 30.1, 8.9.

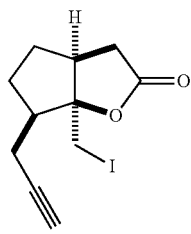

6a-(iodomethyl)-6-(prop-2-yn-1-yl)hexahydro-2H-cyclopenta[b]furan-2-one

General procedure D was applied using tert-butyl 2-(2-methylene-3-(prop-2-yn-1-yl)cyclopentyl)acetate (2.6 mmol, 0.60 g) and 12 (2.6 mmol, 0.65 g). Purification of the crude product by flash column chromatography (20% ethyl acetate in hexane) yielded the two pure diastereoisomers (68% total yield, dr 80:20).

Major diastereoisomer (white solid): M.p. 93-95° C.
$^1$H NMR (300 MHz, CDCl$_3$): δ 3.79 (d, J=10.9 Hz, 1H), 3.42 (d, J=10.9 Hz, 1H), 3.05 (dd, J=18.7, 10.9 Hz, 1H), 2.91-2.78 (m, 1H), 2.50-2.09 (m, 5H), 2.03-1.82 (m, 2H), 1.62-1.44 (m, 2H). $^{13}$C NMR (75 MHz, CDCl$_3$): δ 176.2, 93.7, 82.4, 69.7, 47.3, 44.4, 37.6, 31.9, 31.4, 18.1, 12.4. IR (neat): 3278, 2969, 2928, 2113, 1757, 1449, 1421, 1408, 1249, 1215, 1201, 1164, 1092, 1005, 966 cm$^{-1}$. HRMS (m/z) calcd for C$_{11}$H$_{14}$IO$_2$ ([M+H]$^+$): 305.0033; found: 305.0035.

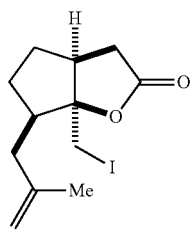

6a-(iodomethyl)-6-(2-methylallyl)hexahydro-2H-cyclopenta[b]furan-2-one

A solution of tert-butyl 2-(3-(2-methylallyl)-2-methylenecyclopentyl)acetate (1.0 equiv, 2.8 mmol, 710 mg) in tetrahydrofuran-water (22 mL of a 3:1 mixture) at 0° C. was treated with sodium bicarbonate (7.0 equiv, 20.0 mmol, 1.7 g) and the resulting mixture was stirred at 0° C. for 15 min. A mixture of potassium iodide (1.2 equiv, 3.4 mmol, 570 mg) and iodine (3.0 equiv, 8.5 mmol, 2.2 g) in water (15 mL) was added to the reaction at 0° C. and the resulting mixture was stirred at room temperature for 1 h. The reaction was poured onto 10% aqueous sodium thiosulfate and the resulting aqueous solution was extracted with diethyl ether. The combined organic extracts were washed with brine, dried (Na$_2$SO$_4$), filtered and concentrated in vacuo. Purification of the crude product by flash column chromatography (20% diethyl ether in hexane) yielded the two pure diastereoisomers (69% total yield, dr 67:33).

Major diastereoisomer (pale yellow oil):
$^1$H NMR (300 MHz, CDCl$_3$): δ 4.81-4.71 (m, 2H), 3.64 (d, J=10.8 Hz, 1H), 3.37 (d, J=10.8 Hz, 1H), 3.03 (dd, J=18.6, 10.8 Hz, 1H), 2.90-2.75 (m, 1H), 2.34-1.80 (m, 6H), 1.73 (s, 3H), 1.60-1.34 (m, 2H). $^{13}$C NMR (75 MHz, CDCl$_3$): δ 176.4, 143.4, 112.2, 94.6, 46.4, 44.0, 37.7, 37.0, 32.2, 31.2, 22.3, 12.3. IR (neat): 2953, 1767, 1646, 1450, 1412, 1242, 1201, 1156, 997, 888 cm$^{-1}$. HRMS (m/z) calcd for C$_{12}$H$_{17}$IO$_2$Na ([M+Na]$^+$): 343.0165; found: 343.0167.

Minor diastereoisomer (yellow solid):

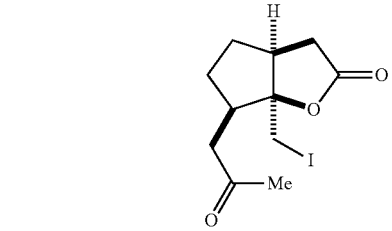

M.p. 38-40° C.
$^1$H NMR (300 MHz, CDCl$_3$): δ 4.80 (s, 1H), 4.72 (s, 1H), 3.60 (d, J=11.0 Hz, 1H), 3.34 (d, J=11.0 Hz, 1H), 3.04 (dd, J=18.6, 10.4 Hz, 1H), 2.71-2.58 (m, 1H), 2.52-2.38 (m, 1H), 2.32-2.08 (m, 3H), 1.99-1.82 (m, 2H), 1.72 (s, 3H), 1.53-1.39 (m, 2H). $^{13}$C NMR (75 MHz, CDCl$_3$): δ 176.2, 142.8, 112.7, 95.2, 47.1, 44.0, 38.1, 37.0, 32.3, 29.4, 21.8, 12.0. IR (neat): 2936, 2877, 1767, 1726, 1650, 1454, 1419, 1230, 1197, 1157, 1112, 992, 889 cm$^{-1}$. HRMS (m/z) calcd for C$_{12}$H$_{18}$IO$_2$ ([M+H]$^+$): 321.0346; found: 321.0350.

6a-(iodomethyl)-6-(2-oxopropyl)hexahydro-2H-cyclopenta[b]furan-2-one

General procedure D was applied using tert-butyl 2-(2-methylene-3-(2-oxopropyl)cyclopentyl)acetate (0.6 mmol, 0.16 g) and I$_2$ (0.6 mmol, 0.16 g). Purification of the crude product by flash column chromatography (20% ethyl acetate in hexane) yielded the two pure diastereoisomers (44% total yield, dr 75:25).

Major diastereoisomer (pale yellow solid): M.p. 75-78° C.
$^1$H NMR (300 MHz, CDCl$_3$): δ 3.56 (d, J=11.1 Hz, 1H), 3.34 (d, J=11.1 Hz, 1H), 3.07 (dd, J=18.7, 10.9 Hz, 1H), 2.89-2.68 (m, 2H), 2.60-2.43 (m, 2H), 2.20-1.85 (m, 6H), 1.61-1.51 (m, 1H), 1.48-1.32 (m, 1H). $^{13}$C NMR (75 MHz, CDCl₃): δ 207.2, 176.4, 94.4, 43.9, 42.9, 42.8, 37.8, 32.4, 31.6, 30.4, 12.6. IR (neat): 2969, 2916, 2850, 1763, 1714, 1412, 1369, 1313, 1248, 1220, 1168, 1041, 1012, 995, 944 cm⁻¹. HRMS (m/z) calcd for $C_{11}H_{16}IO_3$ ([M+H]⁺): 323.0139; found: 323.0144.

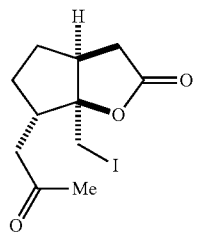

Minor diastereoisomer (white solid): M.p. 115-120° C.

¹H NMR (300 MHz, CDCl₃): δ 3.52 (d, J=11.0 Hz, 1H), 3.24 (d, J=11.0 Hz, 1H), 3.01 (dd, J=18.6, 10.6 Hz, 1H), 2.75-2.56 (m, 3H), 2.44-2.23 (m, 2H), 2.21-1.99 (m, 5H), 1.58-1.44 (m, 1H), 1.40-1.25 (m, 1H). ¹³C NMR (75 MHz, CDCl₃): δ 206.0, 176.0, 94.2, 45.0, 43.7, 42.8, 37.9, 32.3, 30.4, 30.1, 11.9. IR (neat): 2962, 2922, 2851, 1762, 1712, 1415, 1381, 1352, 1239, 1157, 1014, 980, 946, 908 cm⁻¹. HRMS (m/z) calcd for $C_{11}H_{16}IO_3$ ([M+H]⁺): 323.0139; found: 323.0143. X-Ray crystal data available (not shown).

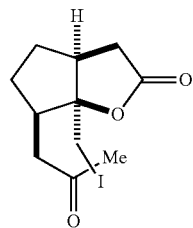

7a-(iodomethyl)-7-(2-oxopropyl)hexahydrobenzo-furan-2(3H)-one

General procedure D was adapted using tert-butyl 2-(2-methylene-3-(2-oxopropyl)cyclohexyl)acetate (1.0 equiv, 0.52 mmol, 138 mg) and 12 (1.1 equiv, 0.57 mmol, 144 mg). Purification of the crude product by flash column chromatography (30% ethyl acetate in hexane) yielded 7a-(iodomethyl)-7-(2-oxopropyl)hexahydrobenzofuran-2(3H)-one (45 mg, 26% yield, white solid). M.p. 123-126° C.

¹H NMR (300 MHz, CDCl₃): δ 3.37 (d, J=11.1 Hz, 1H), 3.29 (d, J=11.1 Hz, 1H), 2.89-2.60 (m, 4H), 2.45 (dd, J=17.8, 9.4 Hz, 1H), 2.26-2.15 (m, 4H), 1.93-1.80 (m, 1H), 1.77-1.59 (m, 2H), 1.49-1.33 (m, 1H), 1.27-1.04 (m, 2HIR (neat): 2946, 2917, 2847, 1773, 1742, 1698, 1412, 1357, 1288, 1190, 1156, 1091, 1008, 943, 916, 893, 840, 762, 695 cm⁻¹. HRMS (m/z) calcd for $C_{12}H_{17}IO_3Na$ ([M+Na]⁺): 359.0115; found: 321.0118.

Performing iodolactonization (general procedure D) directly on the crude compound affords the desired product 7a-(iodomethyl)-7-(2-oxopropyl)hexahydrobenzofuran-2 (3H)-one in 30% isolated yield, over two steps.

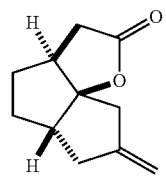

7-methyleneoctahydro-2H-pentaleno[6a,1-b]furan-2-one

General procedure E was applied using iodolactone (minor isomer) (153 mg). Purification of the residue by flash column chromatography (30% diethyl ether in hexane) yielded pure 7-methyleneoctahydro-2H-pentaleno[6a,1-b]furan-2-one (27 mg, 30% yield, pale yellow oil).

¹H NMR (300 MHz, CDCl₃): δ 4.88-4.81 (m, 2H), 2.85-2.28 (m, 8H), 2.11-1.88 (m, 4H). ¹³C NMR (75 MHz, CDCl₃): δ176.6, 147.8, 108.3, 102.3, 48.8, 45.1, 44.8, 38.0, 35.1, 32.5, 31.9. IR (neat): 2949, 2863, 1770, 1663, 1447, 1419, 1253, 1220, 1165, 1024, 980, 968, 899 cm⁻¹. HRMS (m/z) calcd for $C_{11}H_{15}O_2$ ([M+H]⁺): 179.1067; found: 179.1069.

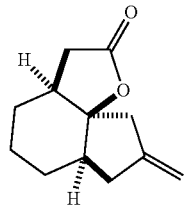

8-methyleneoctahydroindeno[4-b]furan-2(3H)-one

General procedure E was applied using iodolactone 4-allyl-3a-(iodomethyl)hexahydro-1H-inden-2(3H)-one (major isomer) (160 mg). Purification of the residue by flash column chromatography (30% diethyl ether in hexane) yielded 8-methyleneoctahydroindeno[4-b]furan-2(3H)-one (37 mg, 40% yield, yellow oil).

¹H NMR (300 MHz, CDCl₃): δ 5.04-4.81 (m, 2H), 2.78-2.04 (m, 7H), 2.01-1.57 (m, 4H), 1.58-0.97 (m, 3H). ¹³C NMR (75 MHz, CDCl₃): δ 176.8, 145.8, 108.6, 93.7, 45.5, 43.9, 38.5, 37.9, 35.7, 28.8, 24.0, 23.2 IR (neat): 2930, 2858, 1768, 1446, 1424, 1351, 1271, 1229, 1198, 1175, 1153, 1123, 990, 961, 942, 912, 883 HRMS (m/z) calcd for $C_1H_{17}O_2$ ([M+H]⁺): 193.1223 found: 193.1225.

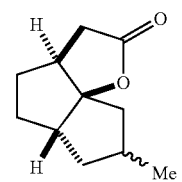

7-methyloctahydro-2H-pentaleno[6a,1-b]furan-2-one

General procedure G was applied using iodolactone (minor isomer) (153 mg). Purification of the residue by flash column chromatography (30% diethyl ether in hexane) yielded 7-methyloctahydro-2H-pentaleno[6a,1-b]furan-2-one as a 67:33 mixture of diastereoisomers (71 mg, 79% yield, colorless oil).

$^1$H NMR (300 MHz, CDCl$_3$): mixture of diastereoisomers: δ 2.78-2.60 (m, 2H), 2.59-2.40 (m, 3H), 2.38-1.86 (m, 12H), 1.66-1.19 (m, 8H), 0.86-0.74 (m, 1H); major diastereoisomer: δ 0.97 (d, 3H, J=5.9 Hz); minor diastereoisomer: δ 1.01 (d, 3H, J=6.3 Hz). $^{13}$C NMR (75 MHz, CDCl$_3$): major diastereoisomer: δ 176.9, 105.6, 51.7, 47.4, 44.6, 41.8, 36.5, 34.8, 32.0, 30.0, 19.0; minor diastereoisomer, characteristic signals: δ 176.7, 48.9, 45.9, 45.6, 39.6, 34.6, 32.9, 32.7, 32.6, 19.0. IR (neat): 2949, 2868, 1767, 1457, 1288, 1222, 1159, 1133, 1090, 1018, 992, 958 cm$^{-1}$. HRMS (m/z) calcd for C$_{11}$H$_{17}$O$_2$ ([M+H]$^+$): 181.1223; found: 181.1224.

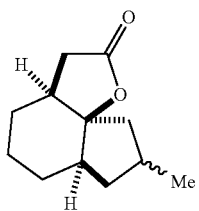

8-methyloctahydroindeno[3a,4-b]furan-2(3H)-one

General procedure G was applied using iodolactone (major isomer) (160 mg). Purification of the residue by flash column chromatography (50% dichloromethane in hexane) yielded 8-methyloctahydroindeno[3a,4-b]furan-2(3H)-one as a 83:17 mixture of diastereoisomers (66 mg, 68% yield, colorless oil).

$^1$H NMR (300 MHz, CDCl$_3$): mixture of diastereoisomers: δ 2.70 (dd, J=16.6, 6.0 Hz, 1H), 2.24-2.04 (m, 6H), 2.01-1.45 (m, 14H), 1.396-1.18 (m, 6H), 1.13-1.00 (m, 8H). $^{13}$C NMR (75 MHz, CDCl$_3$): major diastereoisomer: δ 177.0, 94.9, 46.5, 44.2, 38.7, 38.5, 37.6, 29.4, 28.9, 24.1, 23.4, 22.6; minor diastereoisomer, characteristic signals: δ 45.2, 43.7, 38.5, 38.0, 36.1, 28.9, 28.2, 24.2, 23.5, 22.8. IR (neat): 2928, 2860, 1765, 1445, 1427, 1353, 1279, 1221, 1179, 1168, 1149, 1138, 1054, 940, 928, 903 cm$^{-1}$. HRMS (m/z) calcd for C$_{12}$H$_{18}$O$_2$ ([M+H]$^+$): 195.1380; found: 195.1379.

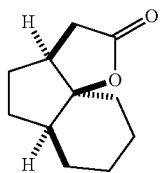

octahydroindeno[7a,1-b]furan-2(3H)-one

General procedure H was applied using iodolactone (major isomer) (153 mg). Purification of the residue by flash column chromatography (20% ethyl acetate in hexane) yielded octahydroindeno[7a, 1-b]furan-2(3H)-one (67 mg, 75% yield, colorless oil).

$^1$H NMR (300 MHz, CDCl$_3$): δ 2.79 (dd, J=17.8, 8.3 Hz, 1H), 2.44-2.34 (m, 1H), 2.34-2.23 (m, 1H), 2.04-1.89 (m, 2H), 1.76-1.20 (m, 11H). $^{13}$C NMR (75 MHz, CDCl$_3$): δ 177.2, 110.0, 48.3, 41.3, 37.1, 34.0, 31.4, 28.5, 25.9, 25.2, 21.7. IR (neat): 2934, 2863, 1760, 1449, 1264, 1204, 1163, 1145, 1130, 1092, 976, 956, 930 cm$^{-1}$. HRMS (m/z) calcd for C$_{11}$H$_{17}$O$_2$ ([M+H]$^+$): 181.1223; found: 181.1224.

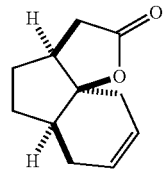

3a,4,5,5a,6,9-hexahydroindeno[7a,1-b]furan-2(3H)-one

General procedure H was applied using iodolactone (major isomer) (150 mg). Purification of the residue by flash column chromatography (40% diethyl ether in hexane) yielded 3a,4,5,5a,6,9-hexahydroindeno[7a,1-b]furan-2(3H)-one (52 mg, 58% yield, colorless oil). HRMS (m/z) calcd for C$_{11}$H$_{14}$O$_2$Na ([M+Na]$^+$): 201.0886; found: 201.0887.

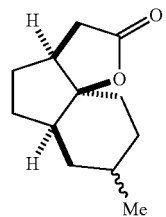

7-methyloctahydroindeno[7a,1-b]furan-2(3H)-one

General procedure H was applied using iodolactone (major isomer) (160 mg). Purification of the residue by flash column chromatography (40% diethyl ether in hexane) yielded 7-methyloctahydroindeno[7a,1-b]furan-2(3H)-one as a 92:8 mixture of diastereoisomers (60 mg, 62% yield, white solid).

$^1$H NMR (300 MHz, CDCl$_3$): δ 2.86-2.73 (m, 2H), 2.39 (ddd, J=10.7, 8.3, 2.3 Hz, 2H), 2.30 (d, J=17.7 Hz, 2H), 2.11-1.88 (m, 4H), 1.76-1.11 (m, 20H), 0.93 (d, J=5.9 Hz, 3H). $^{13}$C NMR (75 MHz, CDCl$_3$): major diastereoisomer: δ 177.2, 95.5, 48.5, 40.9, 37.1, 34.3, 33.6, 32.1, 31.9, 30.4, 28.3, 21.9. IR (neat): 2947, 2919, 2866, 1753, 1214, 1162, 1133, 1091, 998, 931, 692 cm$^{-1}$. HRMS (m/z) calcd for C$_{12}$H$_{19}$O$_2$ ([M+H]$^+$): 195.1380; found: 195.1382. X-Ray crystal data available (not shown).

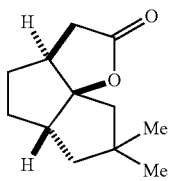

7,7-dimethyloctahydro-2H-pentaleno[6a,1-b]furan-2-one

General procedure H was applied using iodolactone (minor isomer) (0.4 mmol, 126 mg). Purification of the residue by flash column chromatography (40% diethyl ether in hexane) yielded 7,7-dimethyloctahydro-2H-pentaleno[6a,1-b]furan-2-one (50 mg, 50% yield, white solid).

$^1$H NMR (300 MHz, CDCl$_3$): δ 2.79-2.60 (m, 2H), 2.58-2.46 (m, 1H), 2.35-2.23 (m, 1H), 2.05-1.92 (m, 3H), 1.86-1.73 (m, 1H), 1.65-1.37 (m, 4H), 1.08 (s, 3H), 1.04 (s, 3H). $^{13}$C NMR (75 MHz, CDCl$_3$): δ 177.2, 105.9, 52.8, 50.5, 47.6, 45.8, 34.4, 31.0, 29.7, 29.0, 27.0. HRMS (m/z) calcd for C$_{12}$H$_{19}$O$_2$ ([M+H]$^+$): 195.1380; found: 195.1385.

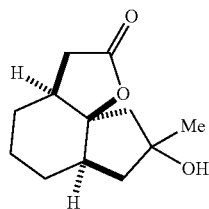

8-hydroxy-8-methyloctahydroindeno[4-b]furan-2(3H)-one

M.p. 85-88° C.

$^1$H NMR (300 MHz, CDCl$_3$): δ 2.70 (dd, J=16.8, 6.1 Hz, 1H), 2.31-2.21 (m, 1H), 2.17-2.03 (m, 3H), 1.93-1.53 (m, 7H), 1.45 (s, 3H), 1.43-1.22 (m, 2H), 1.19-1.00 (m, 1H). $^{13}$C NMR (75 MHz, CDCl$_3$): δ 176.9, 137.9, 95.1, 53.2, 45.6, 44.2, 38.5, 38.3, 31.1, 28.8, 23.9. FTIR (thin film): 3447, 2924, 2861, 1271, 1453, 1369, 1288, 1206, 1156, 1124, 1054, 907, 833, 687, 659 cm$^{-1}$. HRMS (m/z) calcd for C$_{11}$H$_{16}$O$_3$Na ([M+Na]$^+$): 219.09917; found: 219.09923. X-Ray crystal data available (not shown).

3. One Pot Procedures

Iodolactonization—Bu$_3$SnH Mediated Radical Cyclization

To a 0.1 M solution of tert-butyl 2-(3-allyl-2-methylenecyclopentyl)acetate (1.0 equiv, 0.13 mmol) in dry MeCN, 12 (1.0 equiv) was added. After stirring for 1 h at room temperature, dry toluene (13 mL) was added. To the resulting solution at reflux was added dropwise a solution of Bu$_3$SnH (1.1 equiv, 0.14 mmol) and AIBN (0.1 equiv, 0.01 mmol) in toluene (1 mL). The solution was refluxed for 1 h. After cooling to room temperature, the mixture was diluted with diethyl ether, a slight excess of DBU was added, followed by dropwise addition of a 0.1 M ethereal solution of iodine until the iodine color persists. The solution was filtered rapidly through a short plug of silica eluting with diethyl ether. The solution was then concentrated under reduced pressure. GCMS analysis of the crude reaction mixture shows complete conversion to the desired products with a trend comparable to the two steps procedure.

Pain Treatment with Novel Compounds of the Invention

The family of natural agonists of the pain receptor—Transient Receptor Potential Vanilloid 1 (TRPV1) include the exovanilloids, such as capsacin and resiniferatoxin and the exovanilloids, such as is N-Arachidonoyl dopamine. The TRPV1 receptor for noxious heat and several irritants (located at the peripheral terminals of sensory neurons).

The inventors of the present application have found that the compounds of the present application being tricyclic spiranoid lactones could mimic the analgesic effect of the natural TRPV1 agonists.

To examine whether the overlap in the molecular structures of capsaicin and artificial scaffolds of tricyclic angularly fused spiranoid lactones indeed results in TRPV1 activation, a library of synthesized compounds of the invention were screened. Using calcium imaging for rapid indication of TRPV1 activation, four compounds were found to evoke TRPV1 activation (see FIG. 16A).

Figures 16A, 16B, 16C, 16D, 16E:
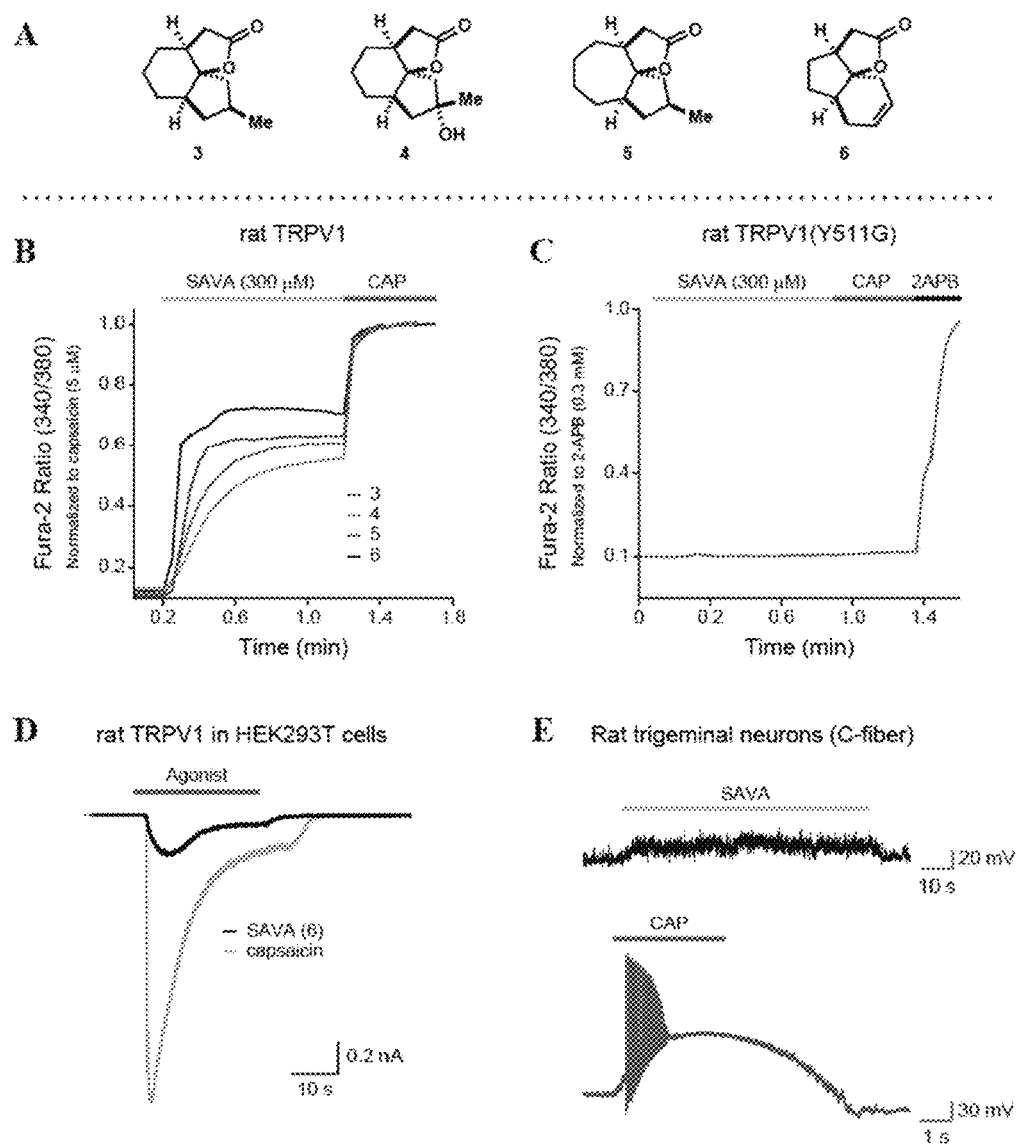
FIGS. 16A-16E. Shows evidence for specific activation of TRPV1 receptor by compounds of the invention. A. Chemical structures of representative tricyclic spiranoid lactones— potential Slow-Acting TRPV1 channels Agonists (SAVA). B. Averaged (n=30 cells) ratiometric calcium responses of HEK293T cells expressing rat TRPV1 (rTRPV1), as a function of time. Application of different SAVA (as indicated; 300 μM; yellow bar) was followed by capsaicin (CAP; 5 μM; red bar). Note, that each SAVA evokes different pattern of activation although all reach similar saturation response that is smaller than capsaicin. C. Same as B, but recorded from HEK293T cells expressing rTRPV1(Y511G) in which VBS domain is mutated. Note, that cells responded to 2-aminoethoxydiphenyl borate (2-APB; 300 μM; black bar), which activates TRPV1 in a VBS-independent manner. D. Superimposed capsaicin-(1 μM; grey line) and SAVA-(compound 6 in B; 300 μM; black line)-induced currents (Vholding=−40 mV) recorded in whole cell configuration from HEK293T cells expressing the rTRPV1. Recording were done on cells with similar TRPV1 expressing levels (determined by the initial response to pH 5.5). Note, the dramatic differences in the activation rate and amplitude. E. Current-clamp recording (I=0) in the whole cell configuration from small-diameter (C-fiber) rat TG neurons (P2 old pup). Upper: SAVA (300 μM; compound 6 in B; yellow bar) lead to a prolonged ~20 mV depolarization with no firing. Bottom: capsaicin (0.2 μM; red) produces pronounced depolarization and burst of action potentials, followed by depolarization block that was maintained as long as the agonist is applied.

These molecules have different activation kinetics and, importantly, none of them elicits the robustness response of capsaicin, even in high concentration (300 μM, see FIG. 16B). To verify, that the evoked response of our TRPV1-positive compounds is through the Vanilloid-binding site (VBS), we analyzed their activation profile on TRPV1(Y511 G) construct.

The inventors have demonstrated that such a point mutation abolishes TRPV1 sensitivity to Vanilloids. The application of novel scaffolds did not affect mutant TRPV1 channels, suggesting that such TRPV1 activation is governed by the VBS (Vanilloid Binding Site), as predicted by SAR (see FIG. 16C). Next, the new scaffolds-evoked TRPV1 currents were analyzed using the voltage-clamp whole-cell configuration of the patch-clamp technique on HEK293T cells stably transfected with the rTRPV1 gene.

It was found that even the most potent of our compounds (depicted from the calcium imaging analysis, 6) evoked dramatically smaller current than capsaicin (see FIG. 16D). Moreover, the activation kinetics was slower than 1 μM capsaicin, even when the 300 μM of SAVA was used (see FIG. 16D).

Thus, these results show that compounds with scaffolds of tricyclic angularly fused spiranoid lactones can serve as TRPV1 agonists through the VBS. These compounds induced lower and smaller effects. It was therefore found that these compounds serve as slow-acting TRPV1 channels agonists.

In dissociated sensory neurons from the trigeminal ganglion (TG) of P2 rat, the inventors have recorded the membrane potential following the application of the different molecules, using current-clamp mode in the whole-cell configuration. As shown in FIG. 16E (lower trace), capsaicin produced a well-described robust depolarization with burst of action potentials followed by depolarization block. In contrast, the compound of the invention have evoked slow (in comparison to capsaicin), ~20 mV depolarization, with no action potential firing (FIG. 16E, upper trace). These preliminary results show that the compounds of the invention exhibit all the characteristics required for slow-acting TRPV1 channels agonists.

The invention claimed is:
1. A composition comprising a compound of general formula (XIV):

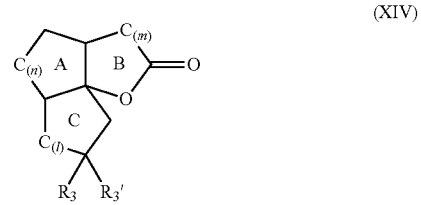

(XIV)

wherein
Ring A is optionally a saturated or unsaturated ring having optionally at least one heteroatom; and is optionally substituted by at least one group selected from straight or branched C$_1$-C$_{10}$ alkyl,-straight or branched C$_2$-C$_{10}$ alkenyl, straight or branched $C_2$-$C_{10}$ alkynyl, CN, —$OR_4$, —$NR_5R_6$, —$C(=O)R_7$, halogen;

$R_4$, $R_5$ and $R_6$ are each independently selected from H, halogen, straight or branched $C_1$-$C_{10}$ alkyl, straight or branched $C_2$-$C_{10}$ alkenyl, straight or branched $C_2$-$C_{10}$ alkynyl;

$R_7$ is selected from H, straight or branched $C_1$-$C_{10}$ alkyl, straight or branched $C_2$-$C_{10}$ alkenyl, straight or branched $C_2$-$C_{10}$ alkynyl, halogen, OH, O($C_1$-$C_{10}$) alkyl, $NH_2$, amine;

n is an integer selected from 1-4;

—$C_{(n)}$— is selected from a straight or branched alkylene, straight or branched alkenylene, straight or branched alkynylene;

m is an integer selected from 1-4;

—$C_{(m)}$— is selected from a straight or branched alkylene, straight or branched alkenylene, straight or branched alkynylene;

l is an integer selected from 1-4;

—$C_{(l)}$— is selected from a straight or branched alkylene, straight or branched alkenylene, straight or branched alkynylene;

$R_3$ and $R_3'$ are each independently selected from C(=O)$R_{20}$, $OR_{21}$, C(=O)$OR_{22}$, $CF_3SO_3$, straight or branched $C_1$-$C_{10}$ alkyl, straight or branched $C_2$-$C_{10}$ alkenyl, straight or branched $C_2$-$C_{10}$ alkynyl;

each of alkyl, alkenyl or alkylnyl groups are optionally substituted by at least one group selected from C(=O)$R_{23}$, $OR_{24}$, halogen, $CF_3SO_3$;

each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, $NH_2$, amine.

2. A composition according to claim 1, wherein m=1, —$C_{(m)}$— being a C1-alkylene.

3. A composition according to claim 1, wherein n=1, —$C_{(n)}$— being $C_1$-alkylene.

4. A composition according to claim 1, wherein n=2, —$C_{(n)}$— being $C_2$-alkylene.

5. A composition according to claim 1, wherein n=3, —$C_{(n)}$— being $C_3$-alkylene.

6. A composition according to claim 1, wherein l=1, —$C_{(l)}$— is a $C_1$-alkylene.

7. A composition according to claim 1, wherein l=2, —$C_{(l)}$— is a $C_2$-alkenylene.

8. A composition according to claim 1, wherein $R_3$ and $R_3'$ are each independently selected from $OR_{21}$, straight or branched $C_1$-$C_{10}$ alkyl, straight or branched $C_2$-$C_{10}$ alkenyl, straight or branched $C_2$-$C_{10}$ alkynyl; each of alkenyl or alkylnyl groups are optionally substituted by at least one group selected from C(=O)$R_{23}$, $OR_{24}$, halogen, $CF_3SO_3$; each of $R_{20}$, $R_{21}$, $R_{22}$, $R_{23}$ and $R_{24}$ is independently selected from H, OH, halogen, straight or branched $C_1$-$C_{10}$ alkyl, straight or branched $C_1$-$C_{10}$ alkoxy, $NH_2$, amine.

9. A compound being selected from:

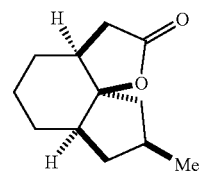

3

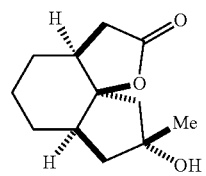

4

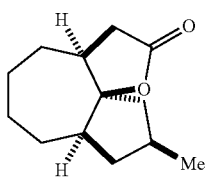

5

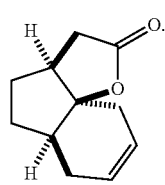

6

10. A method of treating pain and pain related disorders and symptoms in a subject in need thereof, said method comprising administering to said patient a composition according to claim 1.

* * * * *